(12) United States Patent
Komardin et al.

(10) Patent No.: US 6,175,117 B1
(45) Date of Patent: *Jan. 16, 2001

(54) TISSUE ANALYSIS APPARATUS

(75) Inventors: Oleg Komardin, Moscow (RU); Pavel Lazarev, Menlo Park, CA (US)

(73) Assignee: Quanta Vision, Inc., San Mateo, CA (US)

( * ) Notice: Under 35 U.S.C. 154(b), the term of this patent shall be extended for 0 days.

This patent is subject to a terminal disclaimer.

(21) Appl. No.: 09/073,720

(22) Filed: May 6, 1998

Related U.S. Application Data

(63) Continuation-in-part of application No. 09/012,771, filed on Jan. 23, 1998, now Pat. No. 6,054,712, and a continuation-in-part of application No. 09/012,244, filed on Jan. 23, 1998, now abandoned.

(51) Int. Cl.[7] .................................................... G01N 23/04
(52) U.S. Cl. ........................................ 250/363.06; 378/88
(58) Field of Search ........................ 250/363.06, 363.01; 378/88, 90

(56) References Cited

U.S. PATENT DOCUMENTS

| | | | |
|---|---|---|---|
| 3,973,126 | 8/1976 | Redington et al. | 250/444 |
| 4,515,165 | 5/1985 | Carroll | 128/664 |
| 4,549,307 | 10/1985 | Macovski | 378/145 |
| 4,651,002 | 3/1987 | Anno | 250/336.1 |
| 4,751,722 | 6/1988 | Harding et al. | 378/6 |
| 4,754,469 | 6/1988 | Harding et al. | 378/88 |
| 4,807,637 | 2/1989 | Bjorkholm | 128/664 |
| 4,887,285 | 12/1989 | Harding et al. | 378/88 |
| 4,962,515 | 10/1990 | Kopans | 378/37 |
| 4,969,174 | 11/1990 | Scheid et al. | 378/146 |
| 5,150,395 | 9/1992 | Kosanetzky et al. | 378/86 |
| 5,212,719 | 5/1993 | Virta et al. | 378/155 |
| 5,231,652 | * 7/1993 | Harding | 378/86 |
| 5,386,447 | 1/1995 | Siczek | 378/37 |
| 5,491,738 | 2/1996 | Blake et al. | 378/71 |
| 5,604,783 | 2/1997 | Charpak | 378/146 |
| 5,684,851 | 11/1997 | Kurbatov et al. | 378/87 |
| 5,717,733 | 2/1998 | Kurbatov et al. | 378/71 |

FOREIGN PATENT DOCUMENTS

| | | | |
|---|---|---|---|
| 0 402 082 A1 | 12/1990 | (EP) | A61B/6/06 |
| 0 390 653 B1 | 6/1992 | (EP) | A61B/6/00 |
| 0 743 810 A1 | 11/1996 | (EP) | H05G/1/26 |
| 2 299 251 | 9/1996 | (GB) | G01N/23/207 |
| 1402871 A1 | 11/1986 | (RU) | G01N/23/08 |
| 2012872 C1 | 5/1994 | (RU) | G01N/23/02 |
| WO 95/05725 | 2/1995 | (WO) | H05G/1/02 |
| WO 96/23209 | 8/1996 | (WO) | G01N/23/04 |

OTHER PUBLICATIONS

Zheleznaya, L. et al., "X–ray Diffraction Studies on Fine Structure of Mucus Glycoprotein", *Nanobiology*, vol. 1, pp. 107–115 (1992).

Harding, G. et al., "Elastic scatter computed tomography", *Phys. Med. Biol.*, vol. 30, No. 2 (1985), pp. 183–186.

Harding, G. et al., "A K edge filter technique for optimization of the coherent–to–Compton scatter ratio method", *Med. Phys.*, vol. 22, No. 12, Dec. 1995, pp. 2007–2014.

* cited by examiner

*Primary Examiner*—Seungsook Ham
*Assistant Examiner*—Richard Hanig
(74) *Attorney, Agent, or Firm*—Wilson Sonsini Goodrich & Rosati

(57) ABSTRACT

An apparatus for analyzing substances within a breast is disclosed. The apparatus includes a breast positioning area and a beam forming apparatus having a geometry which forms breast penetrating radiation into at least one beam. A detector is configured to detect a scattering pattern of the portion of the breast which scatters radiation from the at least one beam when the breast is positioned within the breast positioning area.

33 Claims, 20 Drawing Sheets

TISSUE ANALYSIS APPARATUS

RELATED APPLICATIONS

This application is a Continuation-in-Part of U.S. applications Ser. No. 09/012,771; filed Jan. 23, 1998, U.S. Pat. No. 6,054,712; entitled A Device for Small Angle Topography and Ser. No. 09/012,244; filed Jan. 23, 1998, now abandoned; entitled Device for Determining Composition and Structure of Inhomogeneous Objects, both of which claim priority to Russian Applications 97107600/25; filed May 6, 1997; entitled A Small-angle Introscopy Technique and a Device Implementing this Technique and 97112038/20; filed Jul. 8, 1997; entitled A Device for Small-angle Mammography and 97113446/14; filed Jul. 31, 1997; entitled Noninvasive Method and Device for Diagnosing Breast Cancers.

Each of the above referenced applications is hereby incorporated by reference as if they were fully set forth herein.

BACKGROUND OF THE INVENTION

1. Field of the Invention

The present invention relates to an apparatus for determining the substances within a bodypart. More particularly, the present invention relates to mammography apparatus for identifying the tissues within a breast.

2. Description of Related Art

The ability to identify substances within a bodypart can be of great value in diagnosing various diseases. For instance, the ability to identify small amounts of cancerous tissues at an early stage of the cancer's development can save the lives of many patients. Identifying cancerous breast tissues at early stages of development has proven very challenging.

Mammography is the standard technique used for identifying cancerous breast tissues. A mammogram is an image of the breast formed by measuring how much each portion of a breast absorbs x-ray radiation. Portions of the breast with an increased absorption of x-rays generally show up as darker areas on the image while portions with a decreased absorption show up as lighter areas. However, different substances can have similar absorptions. Accordingly, the existence of the two substances can be overlooked and the breast misdiagnosed.

To create a mammogram, the breast is placed between two plates which compress the breast. This compression provides the breast with a reasonably uniform thickness through most of the image. The compression of the breast can be painful for the patient.

When a mammography indicates that cancerous tissues may exist a biopsy is frequently performed. The biopsy process includes inserting a needle into the breast to remove a portion of the suspicious tissue. The tissue is sent to a lab so it can be identified. The biopsy procedure can be painful. Further, obtaining the results can be time consuming since they must be sent to a lab.

For these reasons, there is a need for an apparatus which can distinguish between the different tissues within a breast and can eliminate the compression of the breast. There is also a need for an apparatus which can reduce the need for a biopsy and can reduce the time required to identify tissues which may be of interest.

SUMMARY OF THE INVENTION

The invention relates to a mammography apparatus for analyzing substances within a breast. The apparatus includes a breast positioning area and a beam forming apparatus having a geometry which forms breast penetrating radiation into at least one beam. A detector is configured to detect a scattering pattern of the portion of the breast which scatters radiation from the at least one beam when the breast is positioned within the breast positioning area.

The invention also relates to a mammography apparatus for analyzing substances within a breast. The apparatus includes a breast positioning area and a beam forming apparatus having a geometry which forms radiation into at least one beam of radiation. A detector is configured to detect a portion of the beam which is scattered by the breast and a portion of the beam which is transmitted through the breast without being scattered.

The invention also relates to a mammography apparatus for analyzing substances within a breast. The apparatus includes a beam forming apparatus having a geometry which forms radiation from the radiation source into at least one beam of radiation. The apparatus also includes a radiation detector and a filter configured to screen the detector from a portion of the at least one beam which is transmitted through the breast without being scattered.

The invention also relates to a mammography apparatus for analyzing substances within a breast. The apparatus includes a breast positioning area and a beam forming apparatus having a geometry which forms radiation into at least one narrow beam which has a length sufficient to be incident on an entire dimension of the breast. The apparatus also includes a detector configured to detect radiation which has passed through the breast.

The invention also relates to a mammography apparatus for analyzing substances within a breast. The apparatus includes a beam forming apparatus configured to rotate about a longitudinal axis of the beam forming apparatus and having a geometry which forms breast penetrating radiation into at least one beam and a detector configured to receive the at least one beam as the beam forming apparatus is rotated about its longitudinal axis.

The method also relates to a method of identifying the substance within a section of a bodypart. The method includes the acts of determining the scattering pattern of the section of the bodypart and comparing the scattering pattern from the determining act with the scattering patterns of known substances.

DETAILED DESCRIPTION

The invention relates to a mammography apparatus. The mammography apparatus includes an optics assembly with a radiation source and a beam forming apparatus. The beam forming apparatus forms the radiation from the radiation source into a narrow beam of radiation aimed at a breast positioned in a breast positioning area. The beam of radiation passes through the breast. The portion of the breast through which the beam passes is referred to as the analysis area. The optics assembly also includes a two dimensional detector which receives the radiation after the beam passes through the analysis area. As the incident beam passes through the breast, a portion of the incident beam will be absorbed, scattered coherently, scattered incoherently (Compton scattering) and transmitted without being scattered. The portion of the incident beam which passes through the analysis section without scattering is called the transmitted beam.

Figure 20:
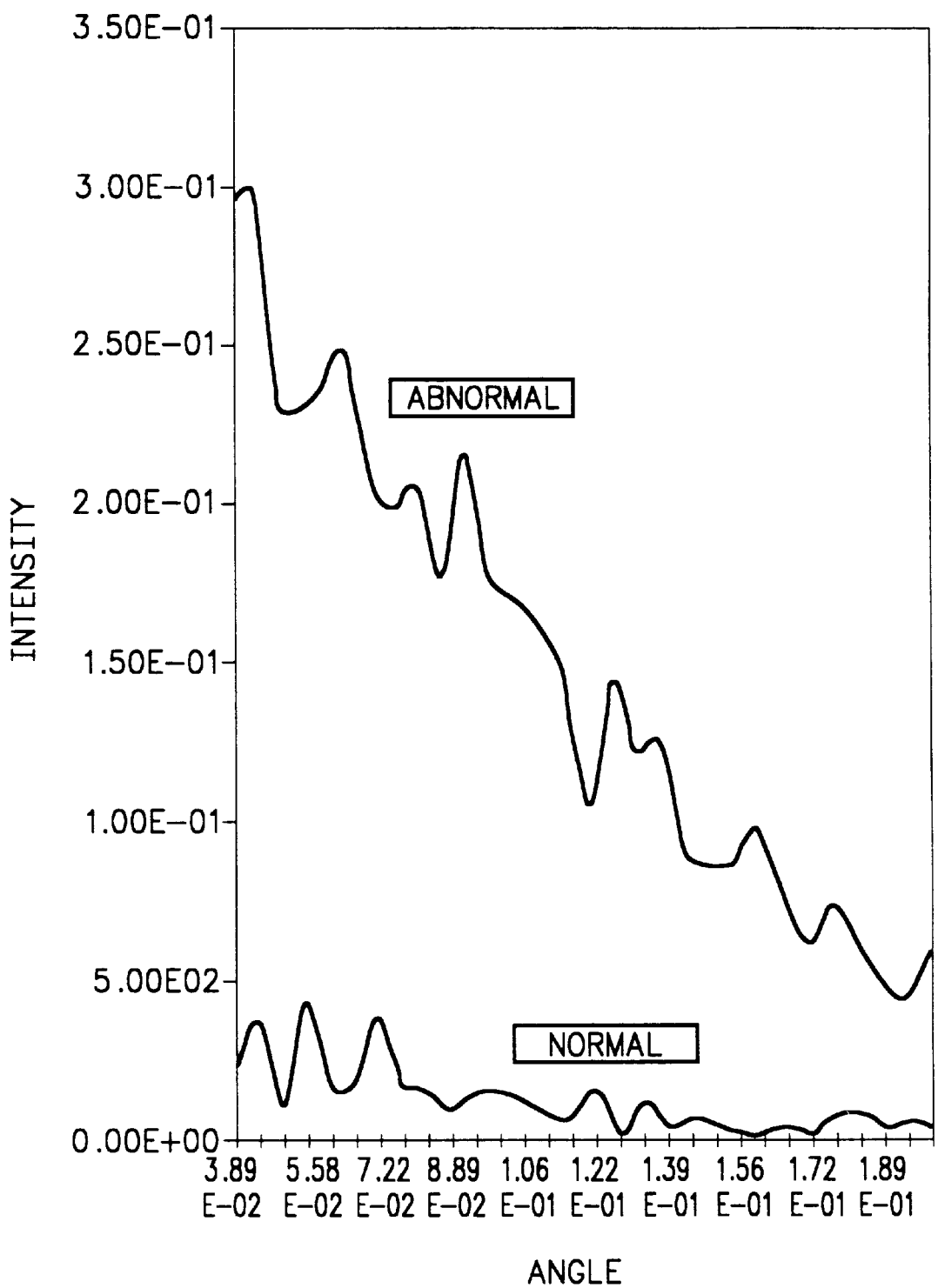
FIG. 20 illustrates the scattering pattern for a sample of normal breast tissue and a sample of malignant breast tissue.

Different substances are known to have unique scattering patterns. For instance, FIG. 20 illustrates the scattering pattern for a sample of normal breast tissue and a sample of malignant breast tissue. The scattering pattern is illustrated as a plot of intensity versus angle. The angle axis refers to the angle between the transmitted beam and the direction a photon was scattered by the tissue. The intensity axis shows the intensity, or amount, of the radiation scattered at the angle on the corresponding angle axis. The relationship between the intensity and the scattering angle for a substance is referred to as that substance's scattering pattern.

The detector included in the optics assembly can detect the angle that a particular photon of radiation has been scattered. This ability is used to determine the scattering pattern of the analysis section. The determined scattering pattern can then be compared with the scattering patterns for known substances. A match between the determined scattering pattern and the scattering pattern for a known substance indicates that the analysis section is made up of the known substance. When the analysis section is composed of several substances, the scattering pattern will be the superposition of the scattering patterns for each of the substances. As a result, the determined scattering pattern can be compared with the scattering patterns for known combinations of substances. Similarly, the scattering pattens of known substances can be superimposed and then compared with the determined scattering pattern. Accordingly, the apparatus can be used to identify the substances which make up the analysis section. As a result, the need for a biopsy can be reduced and perhaps eliminated.

The comparison of scattering patterns can be performed electronically by a processing unit such as a computer. Accordingly, the substances in an analysis section can be quickly identified. Further, breast compression is not necessary for the substances which make up an analysis section to be identified.

The detector can have a resolution which can distinguish photons which are scattered on the order of arc seconds. As a result, the apparatus can measure the small angle scattering pattern for an analysis section. For instance, the scattering pattern can be determined for radiation scattered from as little as one arc seconds to one arc minute and larger. The ability to detect the small angle scattering pattern is important for biological substances. Biological substances are known to exist in lattice states. The displacement between repeating patterns within the lattice is known to be large. Bragg's equation shows that this displacement is inversely related to the scattering angle. Accordingly, biological tissues scatter radiation over small angles on the order of tens of arc seconds.

The use of small angle scattering patterns is advantageous because intensity of scattered radiation tends to increase as the scattering angle decreases. The increased intensity allows the dose administered to the patient to be reduced from the dose which would be required were scattering over larger angles studied.

The optics assembly can be scanned over the breast. During the scan a series of analysis sections can be analyzed. The detector can provide an output to a processing unit. The processing unit determines the substances within each analysis section. The processing unit can include software which combines the results from each analysis section to create a scattering image of the breast. Different substances will likely have different scattering patterns. Because these tissues have different scattering patterns they will show up differently on the scattering image. These substances will show up differently even if the substances have similar absorptions allowing a user to identify tissues which would have been missed with conventional mammography techniques.

The detector can receive at least a portion of the transmitted beam in addition to the scattered radiation. The optics assembly can be scanned over at least a portion of the breast and the output from the detector can be received by a processing unit. The processing unit can compare the intensity of the transmitted beam with the intensity of the incident beam to determine the portion of the incident beam which was absorbed by an analysis section. The processing unit can include software for creating an absorption image from the absorption results. The absorption image can be created by itself or in addition to the scattering image. When a scattering image and absorption image are both created, they can be created from different numbers of analysis sections to provide each image with the desired resolution. The scattering image and absorption image can be compared for similarities and differences.

Embodiments which can detect both transmitted radiation and scattered radiation can be used to eliminate breast compression during a scan. The thickness of the breast at a particular point can be approximated from the amount of absorption of that point during a scan. Each point of the scattering image can then be created by factoring in the approximate thickness at that point. Accordingly, the apparatus can eliminate the need for breast compression.

A filter can be removably positioned between the breast and the detector. The filter can be positioned in the transmitted beam such that the detector is screened from the transmitted beam. Photons in the transmitted beam can be scattered by the media between the breast and the detector. Media which may cause this scattering include, but are not limited to, air and a scintillator which may be present on certain detectors. These scattered photons can be received by the detector, or portion of the detector, which is supposed to received photons scattered by the breast. Accordingly, the photons scattered from the transmitted beam can create noise in a scattering pattern.

The ratio of photons in the transmitted beam to photons scattered by the breast is approximately 100:1. Accordingly, if a small fraction of the transmitted media are scattered by intervening media, the noise created by the transmitted beam can be substantial compared to the signal from photons scattered by the breast. The filter reduces the amount of noise by screening the transmitted beam after it has passed through the analysis section. Reducing the signal to noise ratio also reduces the required dose of radiation which must be given to the patient.

The beam forming apparatus can form the radiation into a plurality of beams incident upon the breast. Accordingly, a plurality of analysis sections are defined. Each of the plurality of beams can be evenly spaced across the breast. During the scan, the optics assembly needs to be moved approximately the distance between adjacent beams in order to scan the entire breast. Accordingly, the scan time is reduced and the opportunity for the breast to move during the scan is also reduced.

Each of the plurality of beams can be incident on the breast at different angles. A scan of the optics assembly over the length of the breast will result in analysis sections which overlap. The detector can be monitored by a processing unit. The processing unit can include tomography software which can form a three dimensional scattering image from the overlapping analysis sections.

The beam forming apparatus can form the beam such that the beam has a length which impinges upon an entire dimension of a breast in the breast positioning area. For instance, the beam can cover the entire width or the entire length of the breast. Accordingly the analysis section can be an entire cross section of the breast. The detector can have a resolution which allows the analysis section to be broken down into smaller test sections. The substances which make up each test section can be identified from the irradiation of a single analysis section.

The optics assembly can also include an adjustable diaphragm which serves to change the length of the beam. Accordingly, the length of the beam can be shortened such that the beam has a dot or square shaped cross section. The dot or square shaped cross section is desirable when suspicious tissues have been identified within the breast. The dot shaped beam is aimed such that the analysis section covers a portion of the suspicious tissue or the entire suspicious tissue. The scattering pattern for that analysis section is formed and the substances within the analysis section identified. Use of the dot shaped incident beam reduces the amount of radiation to which the patient is exposed.

Figure 1:
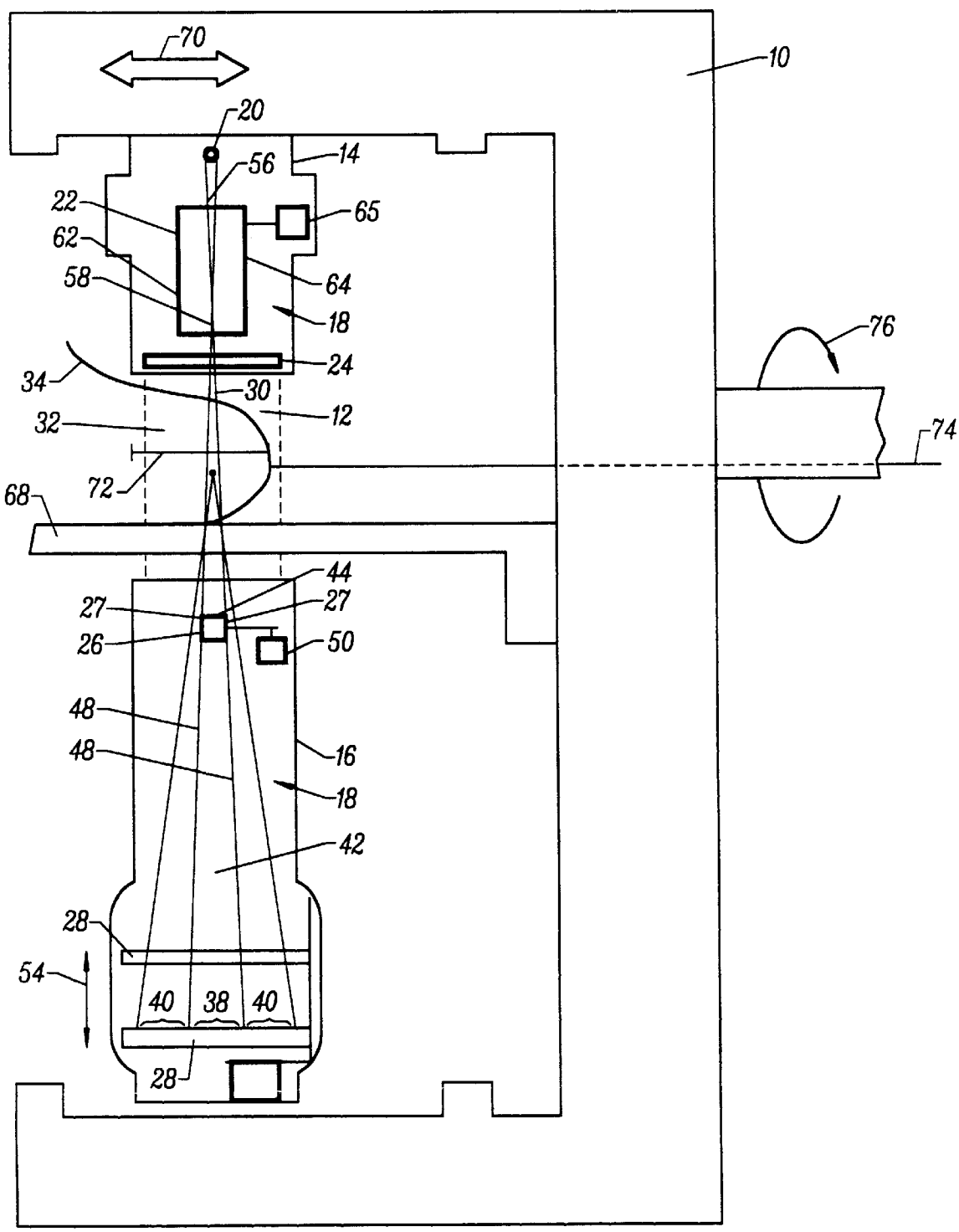
FIG. 1 is a cross section of a frame including an optics assembly according to the present invention.

FIG. 1 illustrates a frame 10 for use in a mammography apparatus. The frame 10 includes a breast positioning area 12, an upper optics housing 14 and a lower optics housing 16. The upper optics housing 14 and the lower optics housing 16 include an optics assembly 18. The optics assembly 18 includes a radiation source 20, a beam forming apparatus 22 and an adjustable diaphragm 24 positioned in the upper optics housing 14. The optics assembly 18 also includes a filter 26 and a two dimensional detector 28 positioned in the lower optics housing 16.

In operation, the beam forming apparatus 22 forms the radiation into a weakly diverging incident beam 30. The incident beam 30 is sufficiently long to be incident on one entire dimension of a breast 32 positioned in the breast positioning area 12. In FIG. 1, the breast 32 is positioned so the incident beam 30 is incident on the entire width of the breast 32, i.e. the length of the incident beam 30 extends into and out of the plane of the page. The beam forming apparatus 22 is preferably positioned around 10 cm from the upper surface 34 of the breast 32. A suitable beam forming apparatus 22 includes, but is not limited to, a Kratki collimator.

The incident beam 30 passes from the beam forming apparatus 22 through the breast 32 to the detector 28. The detector 28 receives radiation in a transmitted beam zone 38 and a scattering zone 40. The transmitted beam zone 38 receives the transmitted beam 42 and the scattering zone 40 receives radiation scattered outside the transmitted beam 42 by the breast 32.

An upper surface 44 of the filter 26 has a shape matching the shape of the cross section of the transmitted beam 42. The filter 26 can be removably positioned in the transmitted beam 42 such that the upper surface 44 is matched to the outer edges 48 of the transmitted beam 42. Suitable materials for the filter 26 include, but are not limited to, leaded glass or metals such as invar which changes shape minimally with changing temperatures. The sides of the filter 26 are optically polished to form a sharp upper edge 27 on the filter 26.

The filter 26 screens the transmitted beam zone 38 from the transmitted beam 42. This screen will cause only scattered radiation which has passed out of the transmitted beam 42 before reaching the filter 26 to be received by the scattering zone 40. The filter 26 can be mechanically moved into the transmitted beam 42 with a micromotor 50. Suitable micromotors 50 include, but are not limited to high precision piezoceramic motors.

To ensure screening of the transmitted beam zone 38, the filter 26 can be positioned in the transmitted beam 42 so the upper surface extends beyond the outer edges 48 of the transmitted beam 42. However, extending the upper surface of the filter 26 beyond the outer edge 48 of the transmitted beam 42 begins to screen the scattering zone 40 from the scattered radiation.

The displacement of the filter 26 from the breast positioning area 12 is a function of the substances being sought within the breast 32. Moving the filter 26 closer to the breast 32 increases the signal to noise ratio. However, this movement also increases the lowest scattering angle which can be measured. Accordingly, when the substances being analyzed have larger scattering angles, the filter 26 can be moved closer to the breast positioning area 12. Suitable displacements of the upper surface of the filter 26 from the breast positioning area 12 include, but are not limited to approximately 250 mm.

The filter 26 can also reduce the dose of radiation absorbed by the patient. Radiation of different wavelengths will have different ratios of scattering to absorption. The filter 26 blocks the transmitted radiation which has absorption information. When the filter 26 is in place, the absorption information may not be of interest. When absorption information is not of interest, the radiation wavelength can be selected with a low ratio of absorption to scattering. The reduced level of absorption results in a reduced dose level to the patient.

The filter 26 need not be entirely opaque but can be partially transmissive. A partially transmissive filter 26 reduces the intensity of the transmitted beam 42 received by the detector 28. Reducing the intensity of the transmitted beam 42 reduces the noise on the detector 28 caused by scattering of the transmitted beam 42 by the air between the breast 32 and the detector 28. The intensity of the transmitted beam 42 can be reduced to the level where the intensity of radiation received by the transmitted beam zone 38 of the detector 28 is the same order as the intensity of the radiation received by the scattering zone 40. The radiation received within the transmitted beam zone 38 can be used to determine the absorption of the analysis section and/or the scattering pattern within the transmitted beam 42. When the scattering pattern is determined within the transmitted beam 42, that portion of the scattering pattern can be added to the scattering pattern from outside the transmitted beam 42 to form the total scattering pattern. Suitable partially transmissive filter materials include, but are not limited to, glass and metal sheets which are thin enough to permit partial passage of the transmitted beam 42.

The detector 28 position adjuster moves the detector 28 relative to the breast 32 as illustrated by the arrow 54. The drive train for the position adjuster can be similar to the drive train used to adjust the height of optics assemblies in photocopiers. Movement of the detector 28 relative to the breast 32 changes the resolution of the detector 28 toward radiation scattered over certain angles. For instance, moving the detector 28 further from the breast 32 increases the area of the detector 28 exposed to radiation scattered over small angles. The larger the detector 28 area exposed to radiation scattered over certain angles, the higher the resolution of the detector 28 with respect to those angles. The detector 28 should be positioned to achieve the desired resolution within the angles of interest. To study radiation scattered over small angles, the detector 28 is preferably positioned approximately 1 meter from the breast positioning area 12. A distance of 1 m between the breast 32 and the detector 28 allows radiation scattered over small angles to exit the transmitted beam 42 before being received by the detector 28. For instance, radiation scattered from 1 arc second within the breast 32 will be scattered over 300 $\mu$m from the center of the transmitted beam 42 when the detector 28 is 1 m from the breast positioning area 12.

The beam forming apparatus 22 can include a first slot shaped aperture 56 and a second slot shaped aperture 58. The width of the incident beam 30 can be adjusted by altering the size of the first and second slot shaped apertures 56, 58. A first side 62 of the beam forming apparatus 22 is fixed while a second side 64 of the beam forming apparatus 22 is mobile. Movement of the second side 64 toward the first side 62 reduces the width of the first and second slot shaped apertures 56, 58 and accordingly, the width of the incident beam 30. Narrowing the width of the incident beam 30 reduces the size of the analysis section but will achieve a higher resolution of the analysis section. Suitable widths for the first and second slot shaped apertures 56, 58 include, but are not limited to 20–120 $\mu$m, 40–80 $\mu$m and 55–65 $\mu$m. The movement of the second side 64 toward the first side can be driven by a micromotor 65.

The breast positioning area 12 can include a breast holder 68 such as a single plate on which the breast 32 is rested. Because the process of identifying the substances which make up an analysis section is not dependent on having a consistent thickness of the breast 32, the compression of the breast 32 which typically occurs in mammography apparatuses can be eliminated. The plate should be transparent to the radiation and cause minimal scattering. In another embodiment the breast positioning area 12 includes a breast holder 68 consisting of an upper plate and a lower plate which can be moved toward one another to compress the breast 32 during the analysis. The plates are constructed from a material which allows the radiation to pass through the plates. Suitable materials for the plate includes, but is not limited to, polyethylene, non-crystalline glass and silicon dioxide. In another embodiment, the breast positioning area does not include any structure for supporting the breast 32. During the analysis the patient need only hold still.

The upper optics housing 14 can be mechanically moved along the frame 10 as illustrated by the arrow 70. The drive train for moving the upper optics can be similar to the drive train used to move an optics assembly in a photocopier. The range of motion covers the entire length 72 of the breast 32 positioned in the breast positioning area 12. The upper optics housing 14 is mechanically coupled to the lower optics housing 16 so the lower optics housing 16 moves with the upper optics housing 14. The movement allows the optics assembly 18 to be scanned along the length 72 of the breast 32. The scan allows analysis of a series of analysis sections which are overlapping or are immediately adjacent to one another. Since a single analysis section can cross the width of the breast 32, a scan over the length 72 of the breast 32 can provide a scan of the entire breast 32.

A scan can be used to provide a scattering image or an absorption image of the breast. During the scan used to create either image, a series of analysis sections are analyzed. When creating the scattering image, suitable separations for each analysis section in the series includes, but is not limited to, 1 mm. The optics assembly should remain in position over each analysis section long enough to deliver a dose of radiation sufficient for formation of a scattering pattern. Suitable times are preferably around 0.1 seconds. If the optics assembly spends 0.1 seconds at each analysis section and each analysis section is 1 mm apart, the total scan time is around 24 seconds for a 240 mm scan. The scan used to create the absorption image can include information from additional analysis sections.

The frame 10 can be rotated about an axis 74 as indicated by the arrow 76. The rotation does not affect the position of the breast 32 or any breast holder 68 within the breast positioning area 12. As a result, the rotation allows a scan and analysis from particular projections. The axis 74 of rotation is as close to the center of the breast 32 as is possible to preserve the distance between the detector 28 and the breast 32 at each projection.

Figure 2:
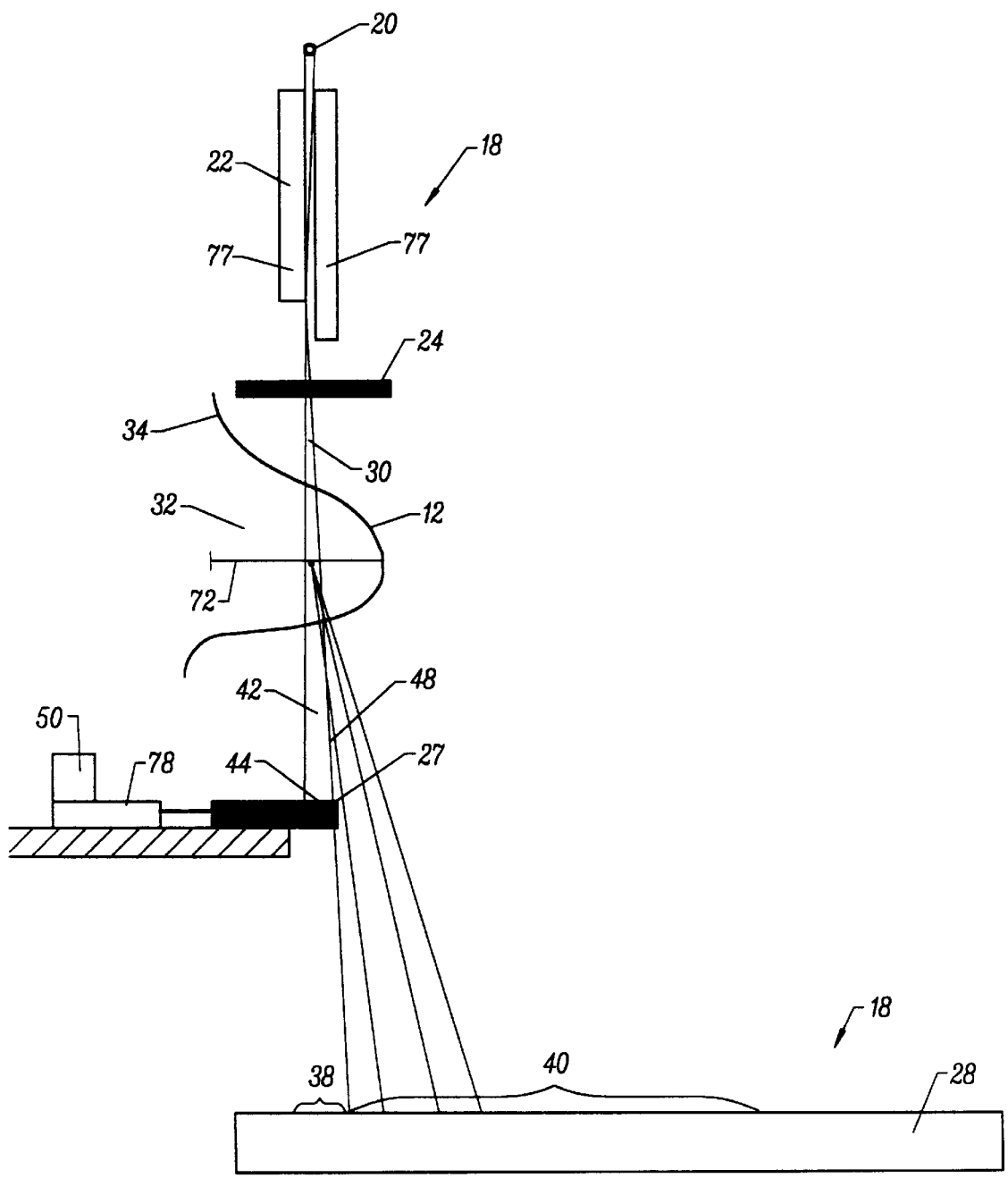
FIG. 2 illustrates an optics assembly including an incident beam aligned with one side of the detector.

FIG. 2 illustrates an embodiment of the beam forming apparatus including opaque sections 77. As illustrated the opaque sections 77 have different lengths. The outer edge 48 of the incident beam adjacent the longer opaque region has a sharper edge. The micromotor 50 is coupled with a drive train 78 which can move the filter 26 in and out of the transmitted beam 42. The filter 26 extends completely through one edge of the incident beam and the filter 26 aligned with the sharper outer edge 48 of the incident beam. Half the scattering zone 40 is screened by the filter 26. However, the scattering pattern on opposing sides of the transmitted beam 42 is symmetrical. Accordingly, the scattering pattern can be developed from one half the scattering zone 40.

The micromotor and drive train can have a placement error on the order of 10 $\mu$m. When the filter 26 is 250 mm from the breast positioning area and the detector is 1 m from the breast positioning area 12, an error of 10 $\mu$m will screen approximately 40 $\mu$m of the scattering zone 40. These 40 $\mu$m correspond to approximately 8 arc seconds on the detector.

Figure 3:
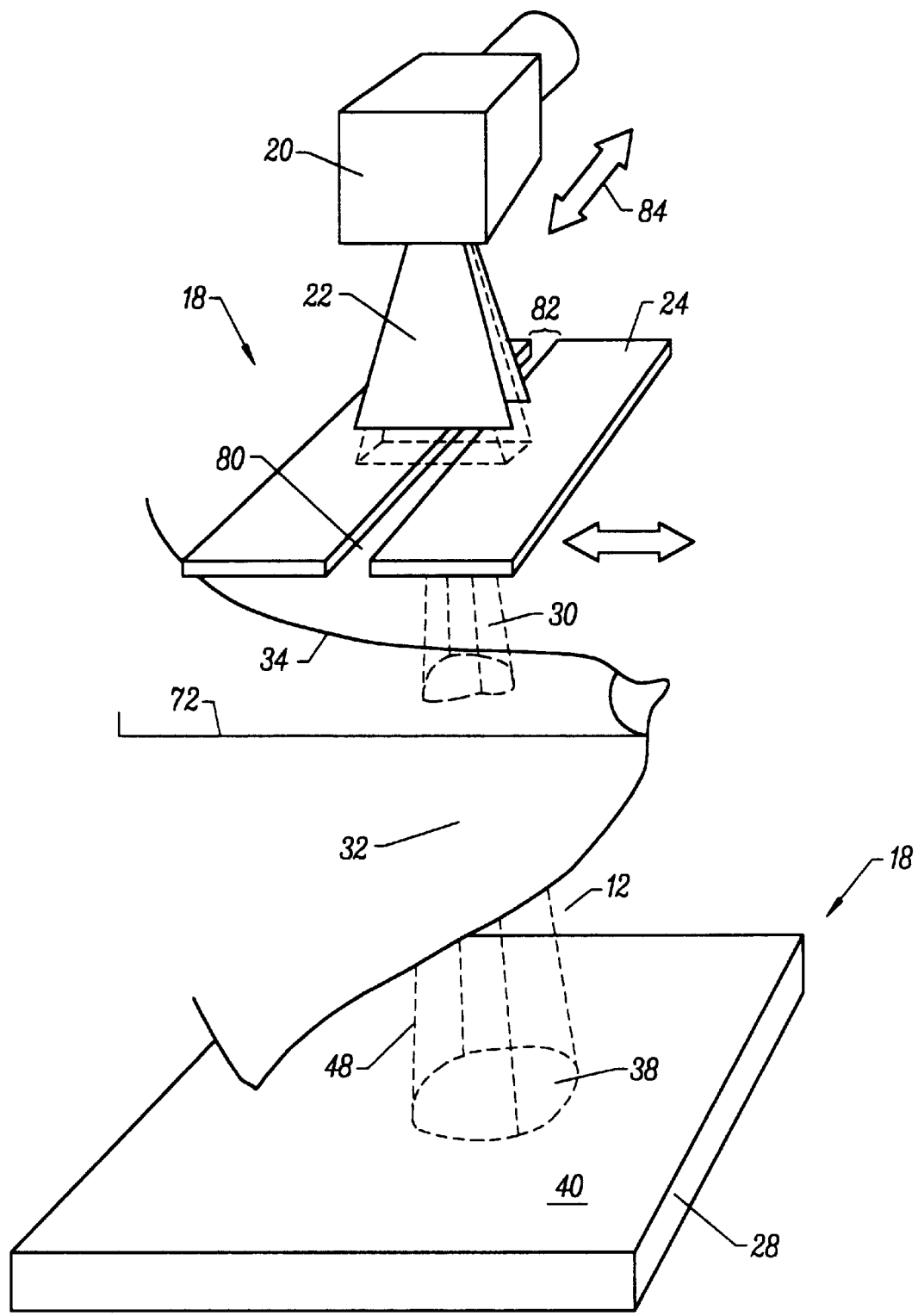
FIG. 3 illustrates an adjustable diaphragm according to the present invention.

FIG. 3 illustrates an adjustable diaphragm 24 for use with the optics assembly 18. The beam forming apparatus 22 forms radiation from the radiation source 20 into a weakly diverging incident beam 30 with a length sufficient to cover the entire length 72 of the breast 32. The adjustable diaphragm 24 is positioned between the beam forming apparatus 22 and the breast 32. The diaphragm 24 includes a slot shaped opening 80 with an adjustable-width 82. The slot shaped opening 80 in the adjustable diaphragm 24 is perpendicular to the length of the incident beam 30. Accordingly, the adjustable diaphragm 24 can be narrowed so the incident beam 30 is formed to a dot or widened so the incident beam 30 is incident along the length 72 of the breast 32.

When the incident beam 30 is formed into a dot, the filter 26 can be changed so the filter 26 extends only trivially beyond the edges of the transmitted beam 42. Accordingly, the detector 28 will receive the radiation scattered over 360°. A dot shaped incident beam 30 is desirable when a particular analysis section has been identified. A small incident beam 30 which can be passed through the analysis section reduces the amount of radiation to which the patient is exposed.

The beam forming apparatus 22 and radiation source 20 can move parallel to the width of the breast 32 as illustrated by the arrow 84. The diaphragm 24 can be moved along the length 72 of the breast 32. Accordingly, the radiation source 20 and diaphragm 24 can be moved so the incident beam 30 penetrates a desired analysis section.

Figure 4:
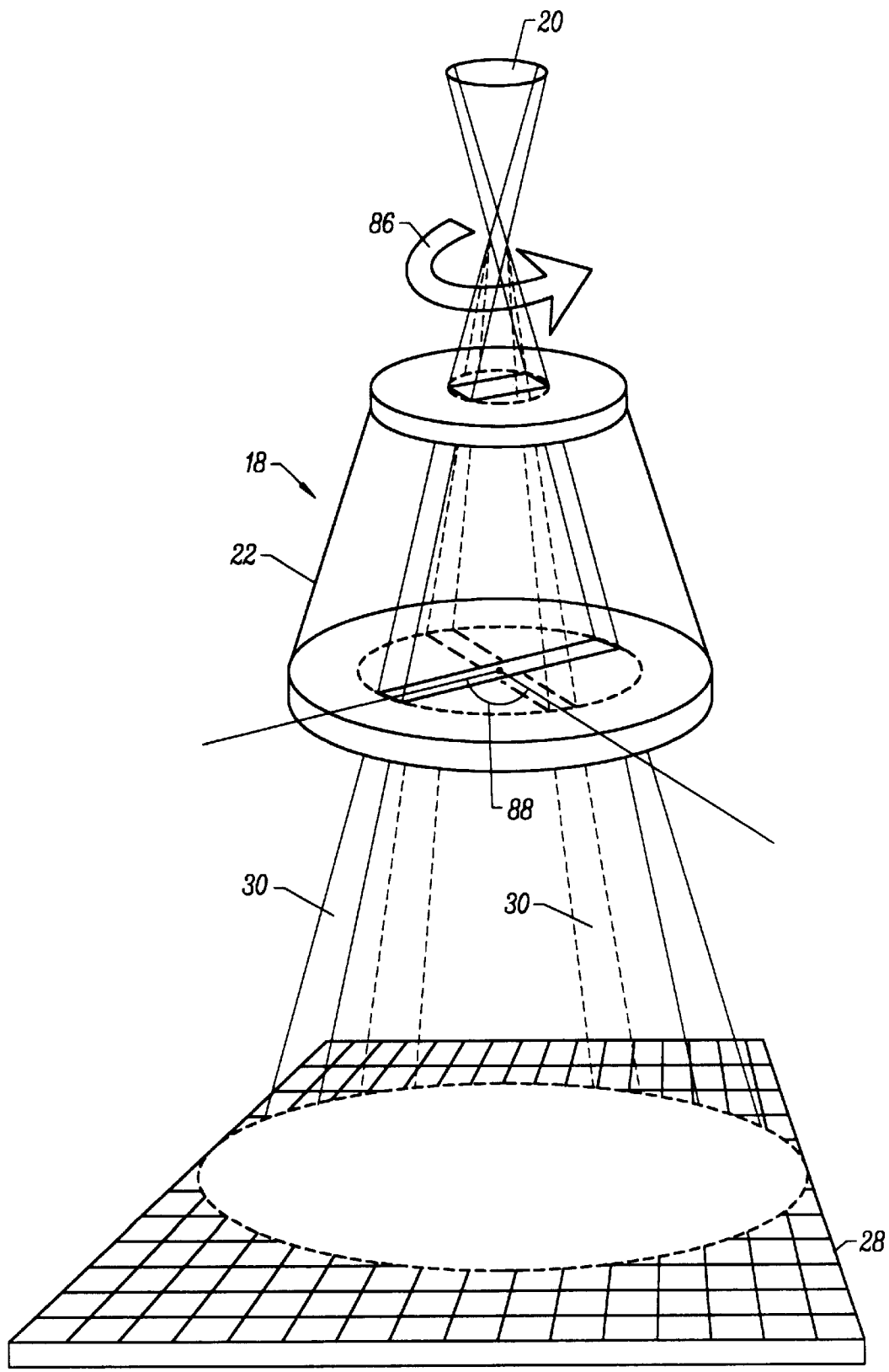
FIG. 4 is sideview of an optics assembly including a beam forming apparatus which can rotate.

As illustrated in FIG. 4, the beam forming apparatus 22 can be configured to rotate about its longitudinal axis as illustrated by the arrow 86. This rotation can be used to analyze substances having anisotropic scattering (diffraction) properties, i.e. having different distributions of electronic density along different directions. When the beam forming apparatus 22 is rotated, the incident beam 30 passes through the object at different azimuthal angles 88. For each azimuthal angle 88 of interest, radiation can be received in the transmitted beam zone 38 and in the scattering zone 40. The change in the scattering pattern as the beam forming apparatus 22 is rotated can be used to determine the spatial distribution of electronic density. This spatial distribution of electron density can then be used to distinguish between similar substances.

The rotation rate of the beam forming apparatus 22 is determined by the exposure time necessary to determine a scattering pattern for an analysis section. The required exposure time can be achieved for one or several revolutions of the beam forming apparatus 22.

Figure 5:
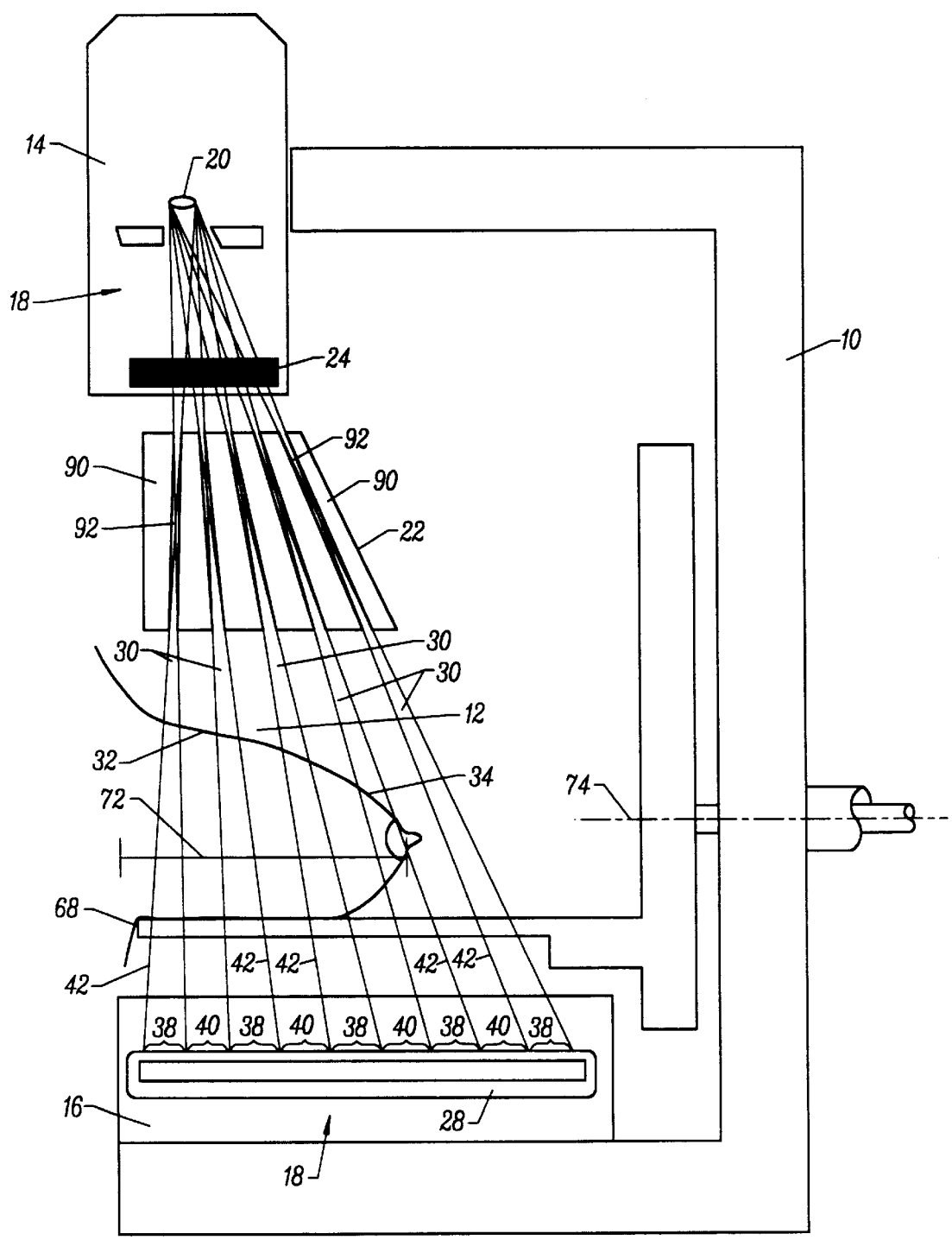
FIG. 5 is a sideview of frame including an optics assembly with a beam forming apparatus for forming radiation from the radiation source into a plurality of beams.

The beam forming apparatus 22 can include a plurality of transparent channels 90 and opaque channels 92 as illustrated in FIG. 5. The radiation from the radiation source 20 passes through the transparent channels 90 to form a plurality of weakly divergent incident beams 30. Each incident beam 30 has a length sufficient to cover the entire width of the breast 32. The beam forming apparatus 22 allows a plurality of analysis sections to be analyzed during a single exposure of the breast 32. Accordingly, the patient's exposure time can be reduced.

The transparent channels 90 of the beam forming apparatus 22 are oriented along directions converging at a point coinciding with the focal point of the radiation source 20. Suitable beam forming apparatuses 22 include, but are not limited to, a slit raster. Further, suitable shapes and arrangements for the transparent channels 90 include, but are not limited to, slits and round apertures located at vertices of hexagonal or square lattices. The transparent channels 90 should converge at the focal spot of the source to increase energy yield of the device. The beam forming apparatus 22 can form incident beams 30 which are spaced along an entire dimension of the breast 32, however, the overlap of scattered radiation from adjacent transmitted beams 42 should be minimized. When the beam forming apparatus 22 is a slit raster, suitable widths for the transparent channels 90 include, but are not limited to 20–120 $\mu$m, 40–80 $\mu$m and 55–65 $\mu$m. When the beam forming apparatus 22 is a slit raster, the width of the opaque sections depends on the desired number of incident beams which are incident on the breast. A suitable width of the opaque section includes, but is not limited to, 0.5 centimeter. When the beam forming apparatus 22 is a slit raster, suitable depths for the transparent channels are on the order of 100 mm depending on the desired divergence of the incident beam. Suitable beam divergences include, but are not limited to 1–10 arc seconds.

The plurality of incident beams 30 can reduce the scan time. For instance, when the incident beams 30 are evenly spaced across the length 72 of the breast 32, the upper optics housing 14 can move a distance roughly equal to the displacement between the incident beams 30 to scan the entire breast 32. This reduced scan time helps to increase the patient's comfort.

Figure 6A:
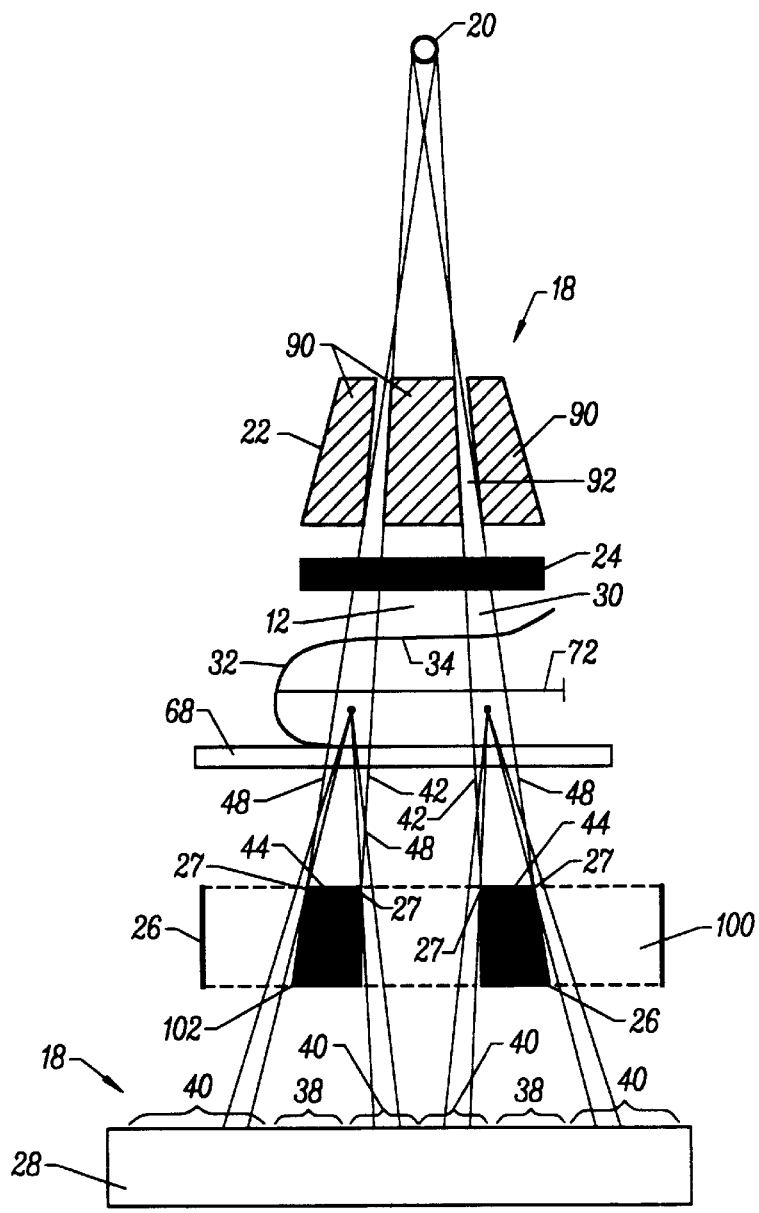
FIG. 6A is a sideview of an optics assembly with a filter including transmissive regions and opaque regions.

As illustrated in FIG. 6A, the optics assembly 18 can include a filter 26 positioned between the breast positioning area 12 and the detector 28. The filter 26 includes transparent regions 100 which transmit the radiation and opaque regions 102 which absorb the radiation. The geometry of the opaque and transparent regions 100, 102 are correlated to the geometry of the beam forming apparatus 22. For instance, when the beam forming apparatus 22 includes slits the filter 26 can be linear raster. When the beam forming apparatus 22 includes cylindrical channels packed in a hexagonal pattern, the filter 26 should have cylindrical shaped opaque regions 102. The width of the opaque regions is a function of the filters position in the transmitted beam 42. The distance between the filter 26 and the breast positioning area is inversely related to the width of the opaque regions.

Figure 6B:
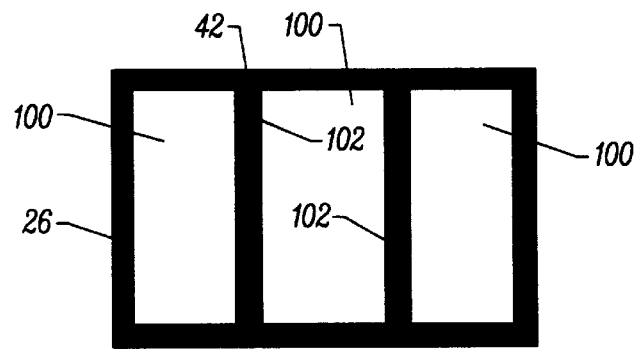
FIG. 6B is a topview of a filter.

FIG. 6B provides a topview of the filter 26. A suitable filter 26 includes, but is not limited to, a 0.5 mm sheet of lead with etched openings which form the transparent regions.

An upper surface 44 of the opaque region 102 is matched to the shape of the cross section of the transmitted beams 42. The upper surface 44 is positioned in the transmitted beams 42 so the scattering zone 40 corresponding to each incident beam 30 is screened from the transmitted beam 42 while the scattering zone 40 corresponding to each incident beam 30 is able to receive scattered radiation. To ensure screening of the transmitted beam 42, the upper surface 44 can extend beyond the outer edge 48 of the transmitted beams 42. However, extending the upper surface 44 beyond the outer edges 48 of the transmitted beam 42 will begin to screen the scattering zone 40 corresponding to each beam from the radiation scattered out of the incident beam.

Figure 7:
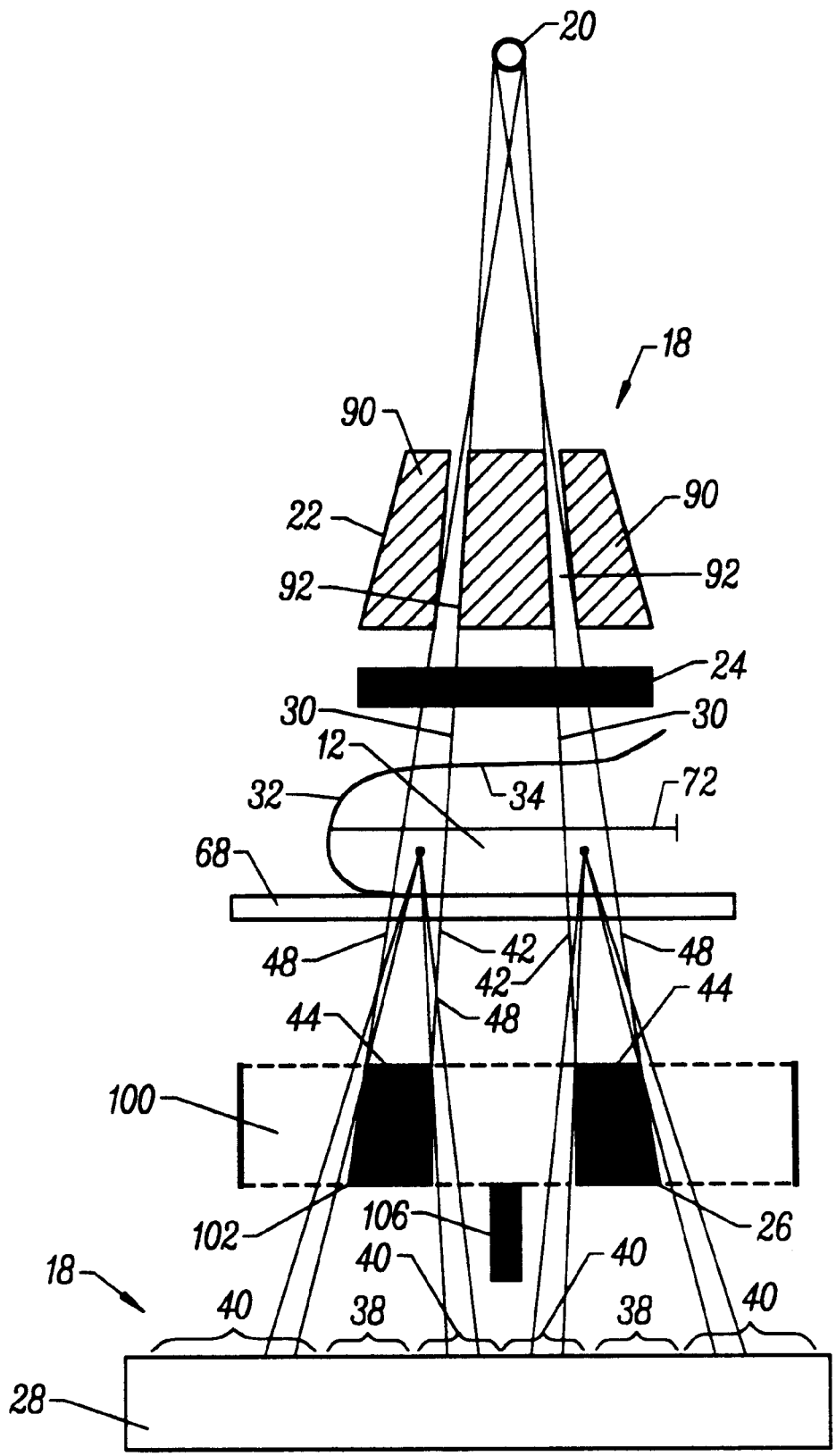
FIG. 7 is a sideview of an optics assembly with a filter including a screening mechanism which reduces overlap of adjacent beams on the detector.

As illustrated in FIG. 7, the filter 26 can include a screening mechanism 106. The screening mechanism 106 has a length and width sufficient to prevent overlap of adjacent transmitted beams 42 on the detector 28.

Figure 8:
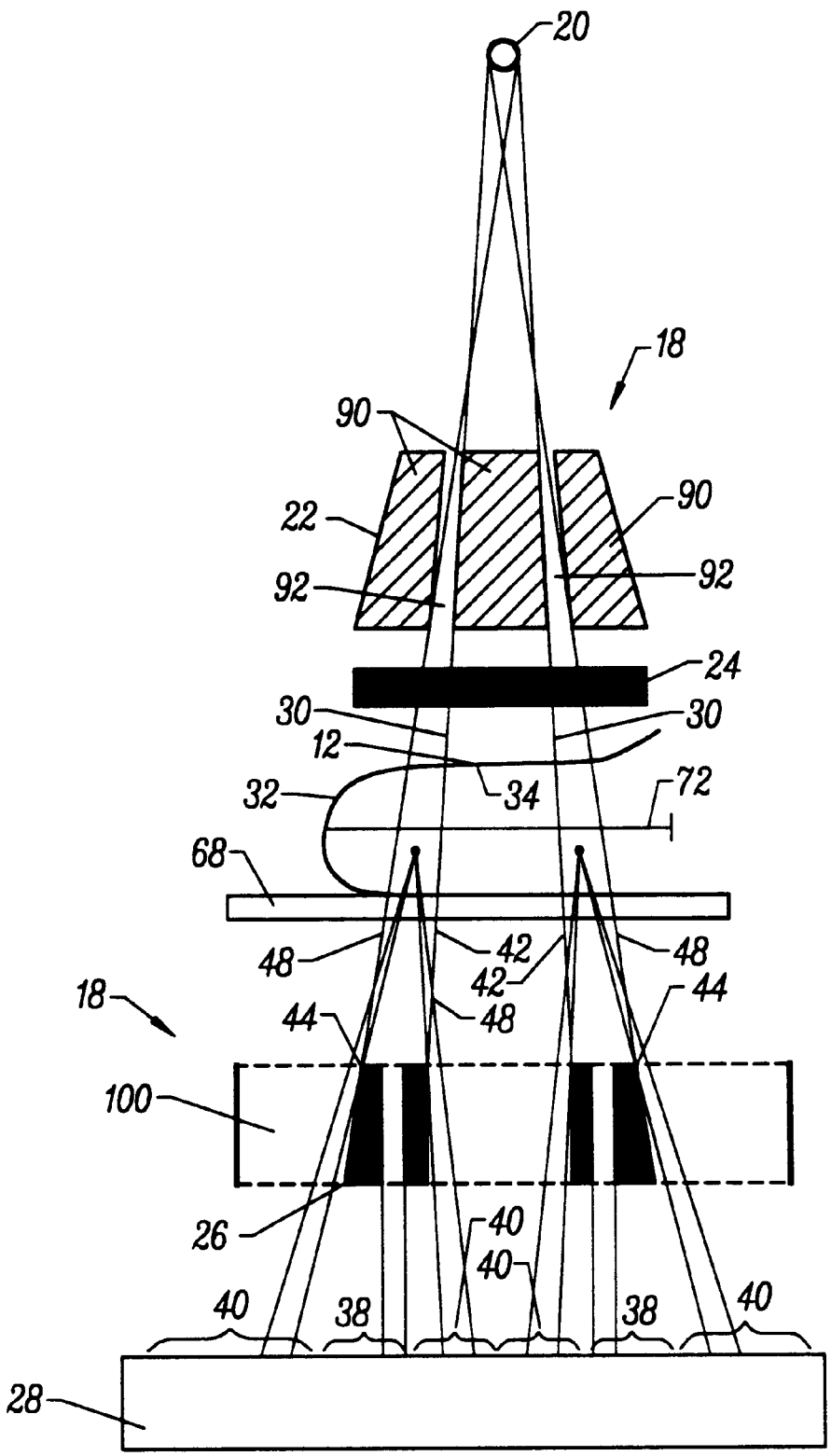
FIG. 8 is a sideview of an optics assembly with a filter including transmitted beam channels which allow at least a portion of the transmitted beam to pass to the detector.

As illustrated in FIG. 8, the opaque regions 102 of the filter 26 can include transmitted beam channels 108. The transmitted beam channels 108 allow at least a portion of the transmitted beam zone 38 to receive at least a portion of the transmitted beam 42. The transmitted beam zone 38 can then be used to determine the absorption of the analysis section.

Figure 9:
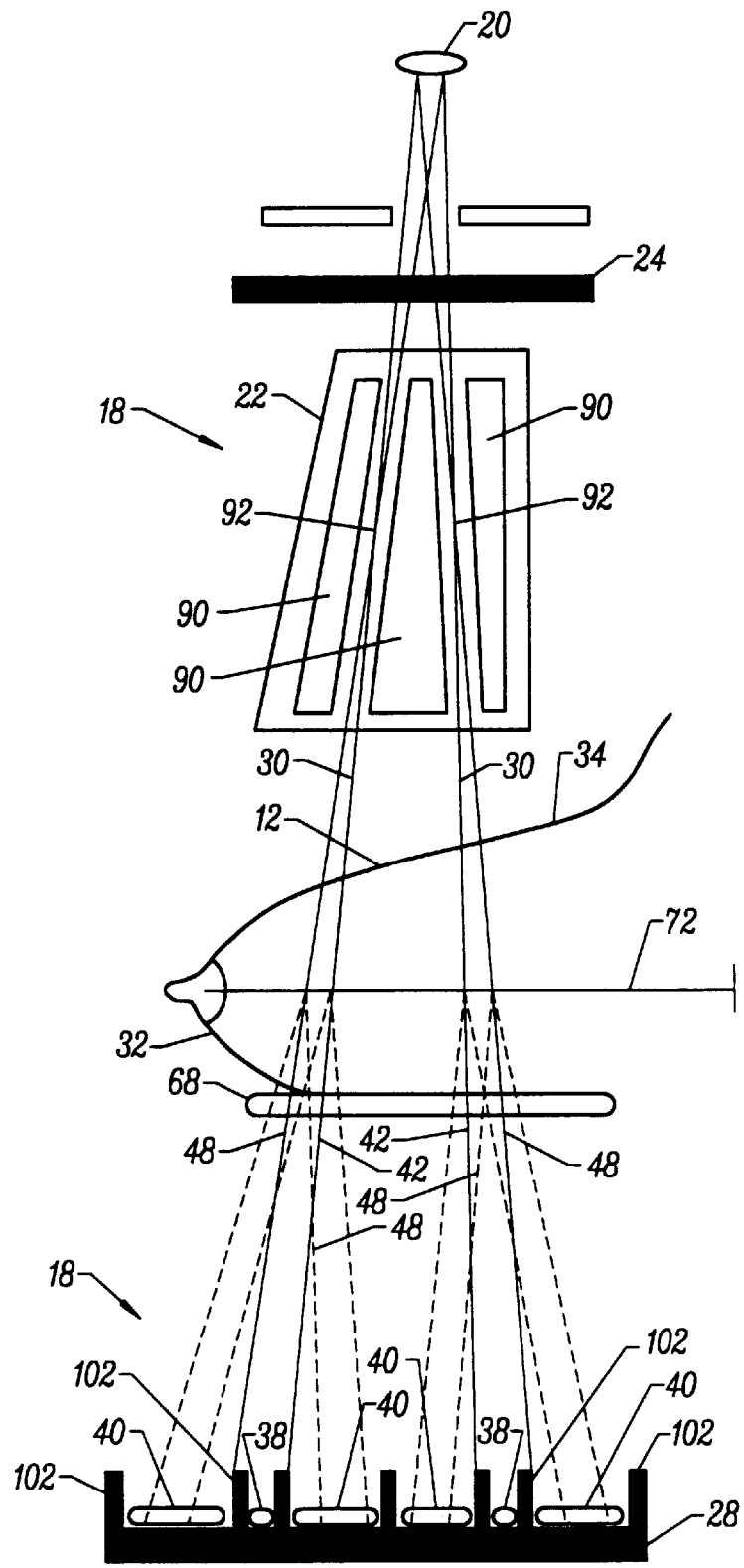
FIG. 9 is a sideview of an optics assembly with a detector including opaque regions configured to screen the scattering region from the transmitted beam.

As illustrated in FIG. 9, the detector can include opaque regions 102. The opaque regions 102 define the transmitted beam zone 38 and the scattering zone 40. An upper surface 44 of the opaque region 102 is matched to the shape of a cross section of the transmitted beams 42. The upper surface 44 is positioned in the transmitted beams 42 so the scattering zone 40 corresponding to each incident beam 30 is screened from the transmitted beam 42 but receives the radiation scattered outside the transmitted beam 42. To ensure screening of the transmitted beam 42, the upper surface 44 can extend beyond the outer edge 48 of the transmitted beams 42. However, extending the upper surface 44 beyond the outer edges 48 of the transmitted beam 42 will begin to screen the scattering zone 40 corresponding to each transmitted beam 42.

The opaque regions 102 positioned between adjacent scattering zones, can have dimensions which reduce interference from radiation scattered from an adjacent incident beam. A suitable height for opaque regions between scattering zones 40 can includes, but is not limited to, flush with the detector elements to 1 mm above the detector elements. A suitable height for opaque regions between a scattering zone 40 and a transmitted beam zone 38 includes, but is not limited to, flush with the detector elements to 1 mm above the detector elements.

Figure 10:
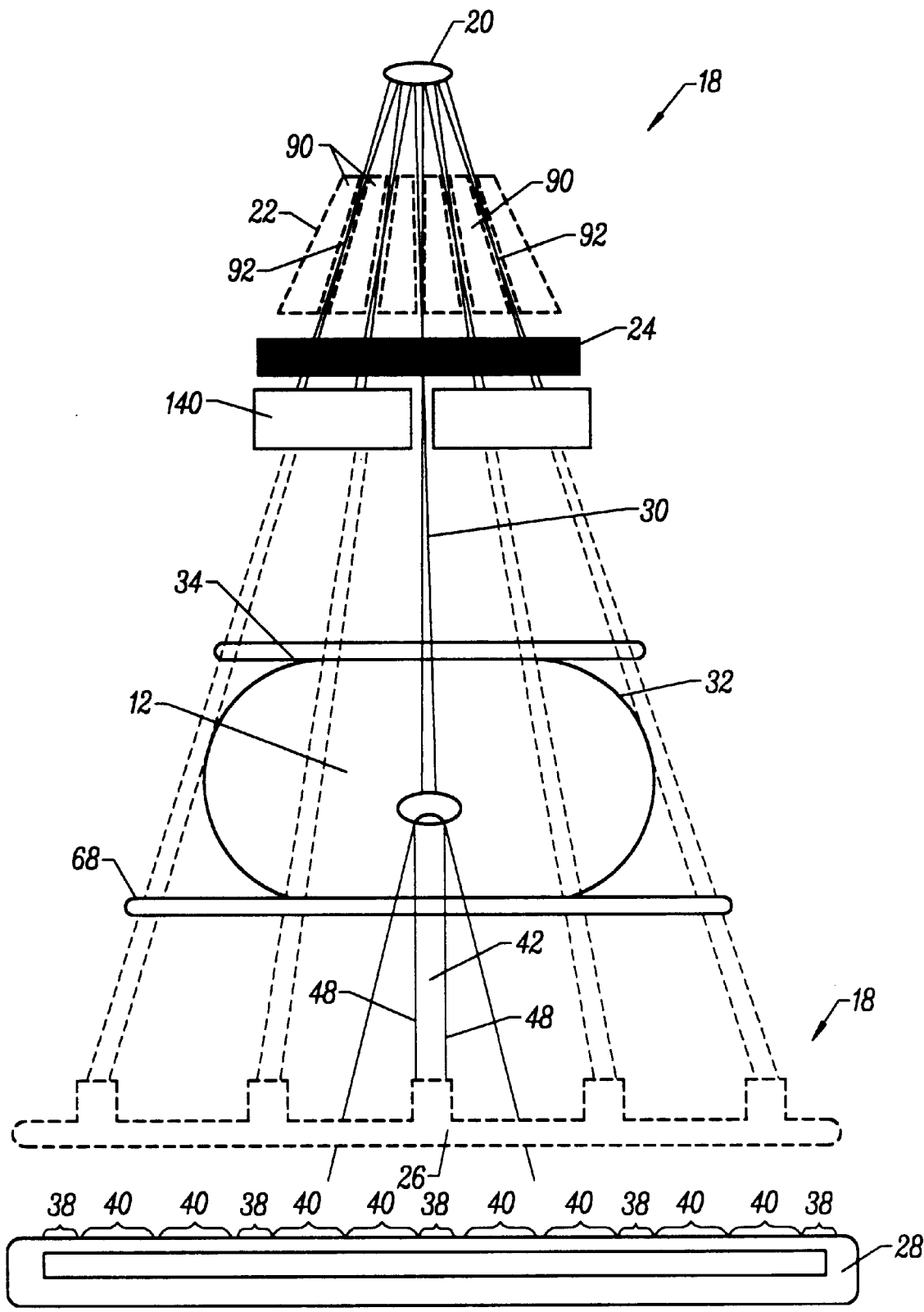
FIG. 10 is a sideview of an optics assembly including a beam filter which screens the breast from radiation beams which are not currently of interest.

As illustrated in FIG. 10, a beam filter 140 can be positioned between the beam forming apparatus 22 and the breast positioning area 12. The beam filter 140 screens the breast 32 from incident beams 30 which are not of interest. For instance, when a particular analysis section has been identified, the beam filter 140 can be positioned in front of incident beams 30 directed toward analysis sections which are not of interest. The adjustable diaphragm 24 can be used to adjust the incident beam 30 to the desired length.

Figure 11:
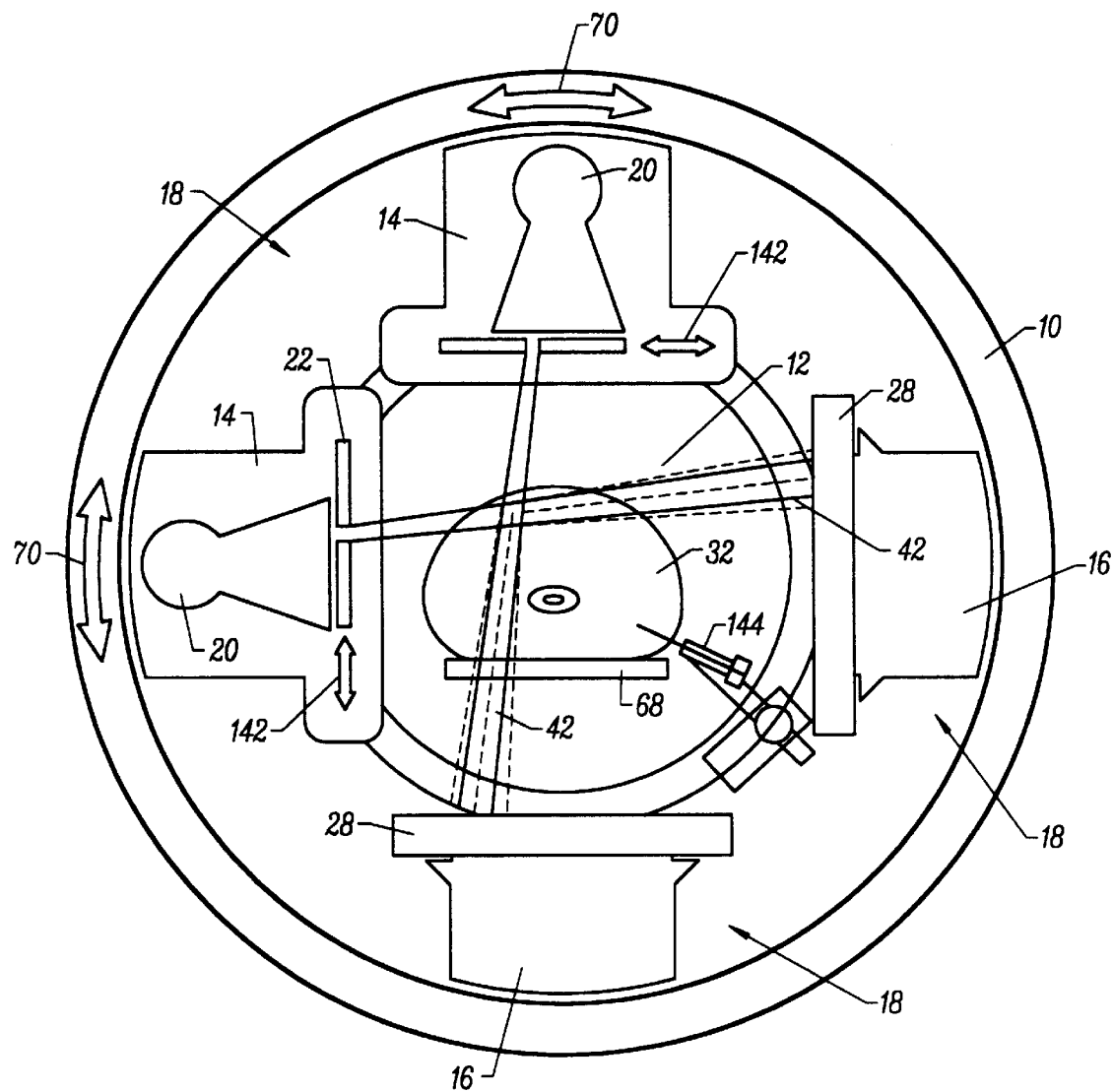
FIG. 11 illustrates a frame including two optics assembly.

FIG. 11 illustrates another embodiment of a frame 10. The frame 10 include two optics assemblies 18 which can be independently moved around the frame as illustrated by the arrows 70. Each optics assembly 18 includes a beam forming apparatus 22 and a radiation source 20. Each beam forming apparatus 22 forms an incident beam 30 with a length sufficient to cover the length 72 of the breast 32. The beam forming apparatus 22 can be moved in front of the radiation source 20 as illustrated by the arrows 142. The motion of the beam forming apparatus 22 causes the incident beam 30 to be scanned across the width of the breast 32. The results of the scan for both optics assemblies 18 can be used to form the scattering image in three dimensions. Because the scattering image is formed from the results of two scans taken from different projections, the scattering image will have a resolution which is higher than the scattering image produced from a single scan. This high resolution can be used to precisely identify the position of suspicious tissues within the breast.

The frame 10 of FIG. 11 can be used with a biopsy device 144 for sampling the suspicious tissue. The biopsy device 144 can be aimed at the suspicious tissues identified during the first scans. Once the biopsy device 144 is positioned within the breast 32, the biopsy device 144 can be more precisely positioned by performing additional scans to form additional scattering images. The biopsy device 144 shows up in the additional scattering imaged and can be moved closer to the suspicious tissue in response to the position of the biopsy device on the scattering image.

The detector 28 can be photographic film. The tissues of an analysis section can be identified by manually comparing the scattering pattern on the exposed photographic film to previously exposed photographic films corresponding to analysis sections with known substances.

Figure 12:
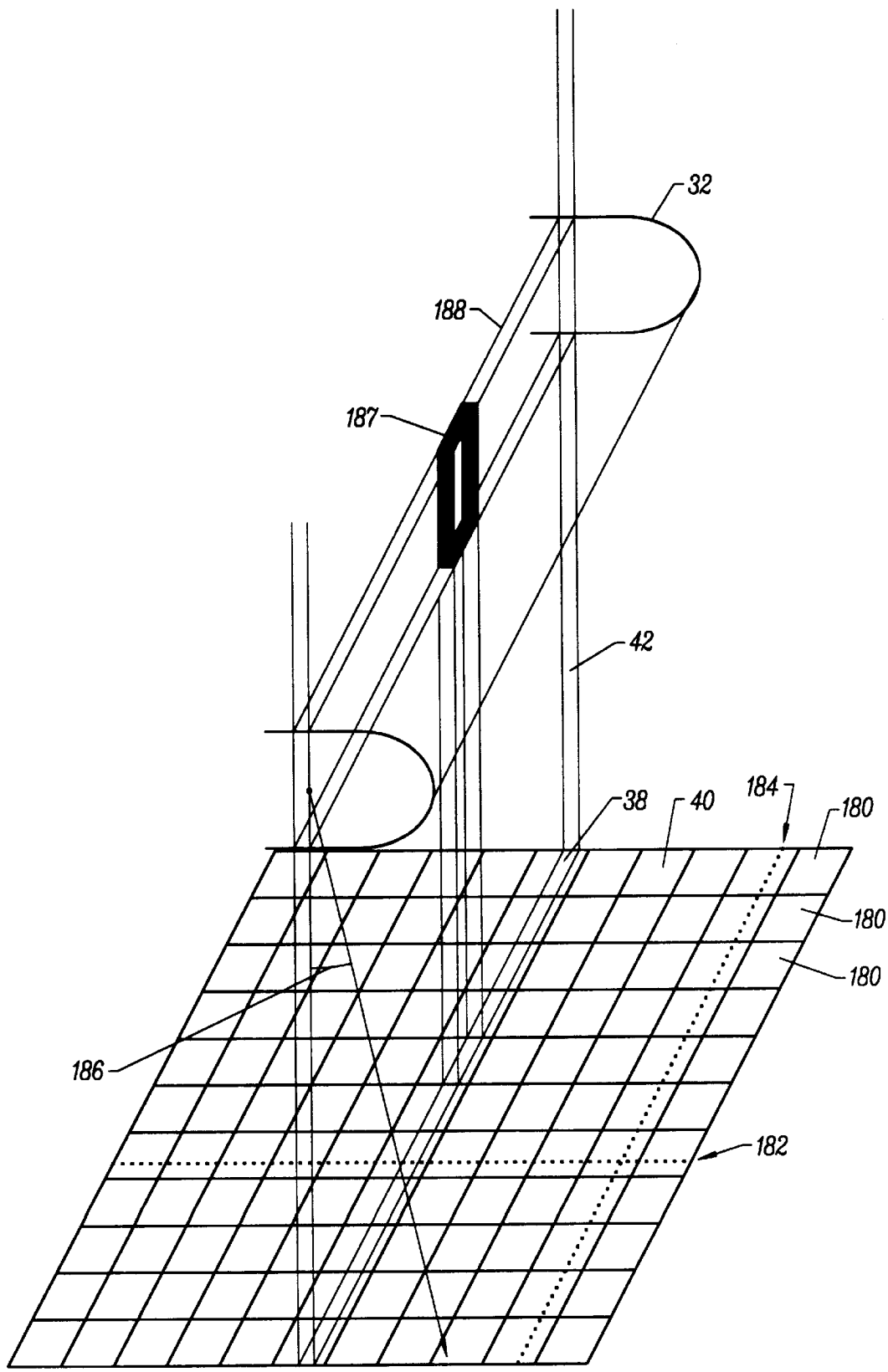
FIG. 12 illustrates a detector including an array of detector element.

The detector 28 can include an array of detector elements 180 as illustrated in FIG. 12. The detector elements 180 are illustrated as aligned in rows 182 and columns 184 on the detector 28 but in some embodiments the detector elements 180 can be aligned in a circular array or can be shaped as concentric circles. A photon of radiation striking a substance in the analysis section is scattered by some angle 186. The angle 186 of scattering is a function of the substance and the energy of the photon. As illustrated, a scattered photon will strike a particular detector element 180. Accordingly, there is a relationship between the detector element 180 which receives a photon and the approximate angle 186 which the photon was scattered. This relationship is used to determine the scattering pattern of the analysis section.

The radiation scattered by a single analysis section can be received on several rows of the detector. The scattering pattern can be determined for each row. Accordingly, each row of detectors defines a tested section 187 within the analysis section 188.

The detector elements 180 can have dimensions of around 10 $\mu$m. Although FIG. 12 illustrates a single column of detector elements 180 as receiving the transmitted beam 42, smaller detector element 180 dimensions permits several detector elements 180 to receive the transmitted beam 42. When the detector 28 is 1 meter from the breast 32, a single detector element 180 will be exposed to radiation scattered over approximately 2 arc seconds. The average size of a film used in mammography is approximately 180 mm×240 mm. Accordingly, the total length of the columns can be around 180 mm and includes approximately 18,000 detector elements 180. As a result, a single analysis section can include up to 18,000 tested sections 187. Since the total length of the columns is around 180 mm the beam can have a length around 180 mm. Suitable lengths for the beam include, but are not limited to, 100 mm–300 mm and 180 mm to 240 mm. Accordingly, the ratio of the beam width to length can be on the order of 0.0001:1.

The length of the rows 182 depends on the desired angular range of the scattering pattern and the distance between the breast 32 and the detector 28. For instance, when the beam forming apparatus 22 is designed to produce a single beam and the detector 28 is positioned 1 meter from the breast 32, the detector 28 should be approximately 5 $\mu$m wide for every arc second of the scattering pattern to be obtained. The 5 $\mu$m number assumes detector elements 180 on only one side of the center of the transmitted beam 42 will be used to detect the scattering pattern, however, when both sides are used the number should be around 10 $\mu$m. Further, the scattering pattern range can be increased by aligning the transmitted beam 42 with one end of the detector as illustrated in FIG. 2. Suitable scattering pattern ranges for identifying substances in breasts include, but are not limited to, zero arc seconds to two degrees, zero arc seconds to one degree, zero arc seconds to ten arc minutes and zero arc seconds to one arc minute.

The detector elements 180 can be different depending on their function on the detector 28. For instance, the detector elements 180 within the scattering zone 40 of FIG. 9 are used to develop a scattering pattern. Development of scattering patterns requires a high resolution. Further, the scattered radiation can have a low intensity. Accordingly, the detector elements 180 within the scattering zone 40 must be small and highly sensitive. The detector elements 180 within the transmitted beam zones 38 of FIG. 9 can be used to measure both the absorption and scattering pattern of the analysis section, however, they can also be used to measure only the absorption characteristics of the analysis section. Absorption measurements require a low level of resolution. Further, the transmitted beam 42 will have a higher intensity than the scattered beams. Accordingly, when the detector elements 180 within the scattering zone 40 of FIG. 1 are used to measure only the absorption pattern of the analysis section, the detector elements 180 can be larger and have a reduced sensitivity.

The scattering angle of a photon depends on the energy of the incident photon. As a result, polychromatic radiation can result in a complex scattering patterns. The complexity can be considerably reduced with monochromatic radiation. Suitable wavelengths for radiation in the incident beam includes, but is not limited to 0.71 Å $K_\alpha$ Mo, 0.3 Å Ag and 0.1 Å W. Suitable radiation sources include, but are not limited to, x-ray tubes.

The complexity of scattering patterns can also be reduced when polychromatic radiation is used. For instance, a filter which screens the wavelengths which are not of interest can be used. Further, the scattering pattern energy sensitive detector elements 180 can be used. Energy sensitive detector elements 180 can provide identifiably different signals based on the energy of the photon received. Accordingly, the scattering pattern can be developed from signals which are derived form photons having identical energies. Suitable detector elements 180 include, but are not limited to, charge coupling devices, photodiode, thallium activated sodium iodide detectors 28 and semiconductor detectors 28 such as germanium detectors 28 or scintillation detectors 28. A suitable detector 28 can be purchased from Photonics Corporation, Metorex Corporation, General Electric Corporation and Toshiba Corporation.

Figure 13:
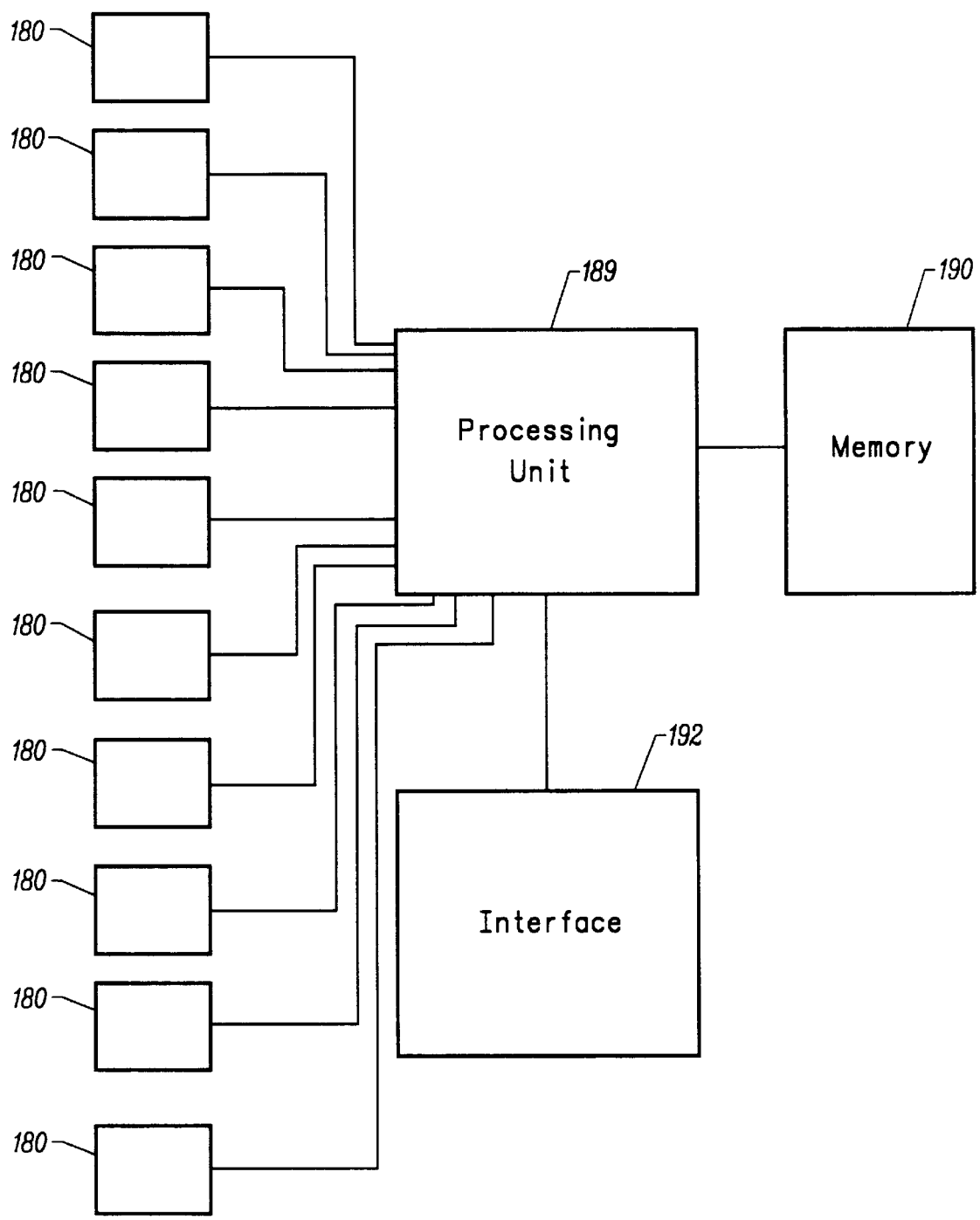
FIG. 13 is a schematic of a mammography apparatus.

FIG. 13 provides a schematic of a mammography apparatus. The apparatus includes a plurality of detector elements 180, a processing unit 189, a memory 190 and a user interface 192. The user interface 192 can include conventional interface 192 tools such as keyboards and one or more monitors so the user can view scattering images, absorption images and other output. The processing unit 189 receives signal from the detector elements 180. The processing unit 189 processes the signals and provides the results to the user on the user interface 192. Suitable processing units 180 include, but are not limited to, a Sun Workstation.

Figure 14:
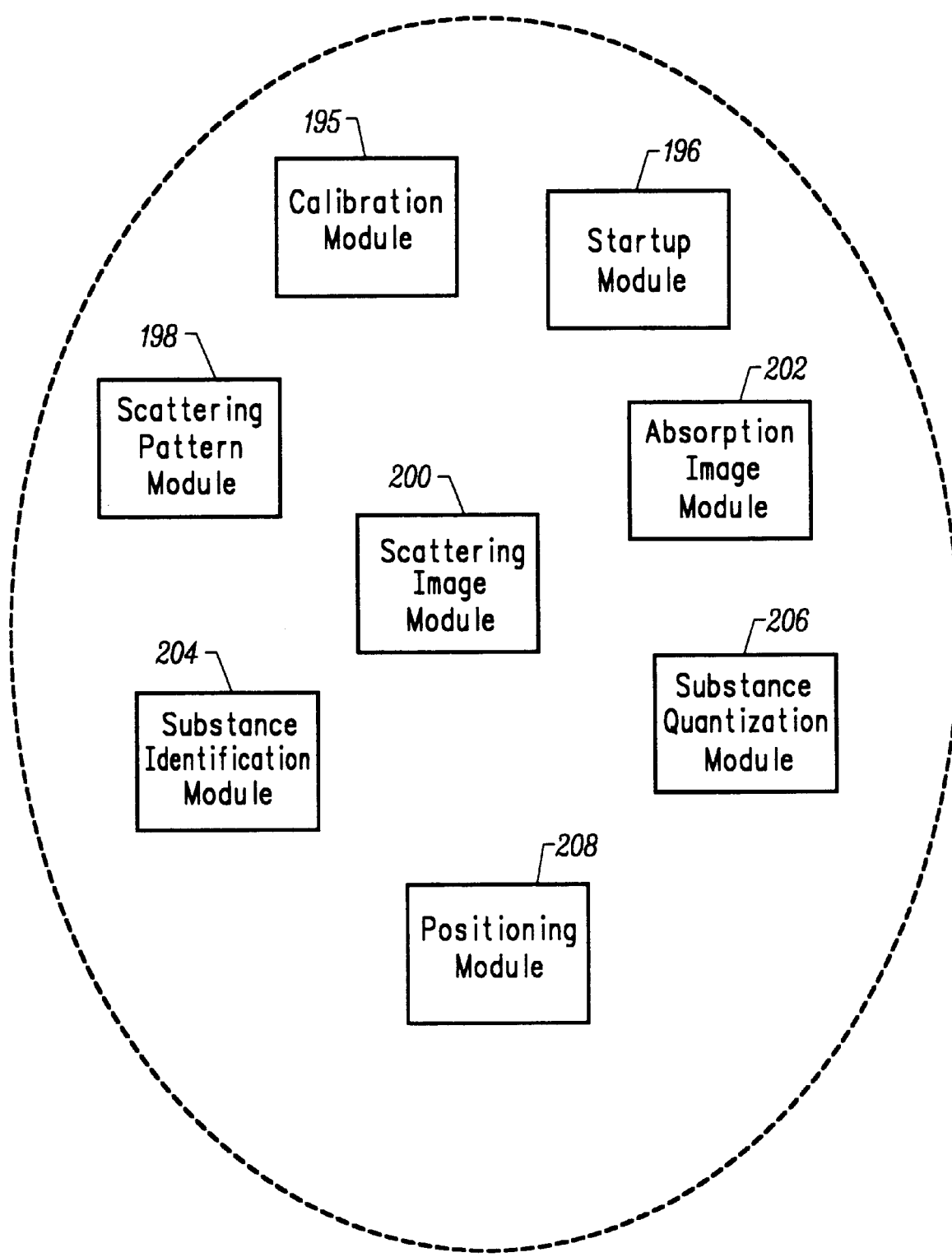
FIG. 14 illustrates software modules stored in the memory.

As illustrated in FIG. 14, the memory 190 includes a number of software modules which are accessed by the processing unit 189. The memory 190 includes a alignment module 195, a startup module 196, a scattering pattern module 198, a scattering image module 200, an absorption image module 202, a substance identification module 204, a substance quantization module 206 and a substance positioning module 208. The modules can be accessed in any order and one software module is able to call another.

The alignment module 195 is accessed whenever the filter and beam forming apparatus may have become out of line. The processing unit 189 activates the micromotor 50 which removes the filter 26 from the transmitted beam 42. The incident beam is formed without the breast being positioned within the breast positioning area 12. The detector elements 180 within the transmitted beam zone 38 are identified by identifying the detector elements 180 receiving radiation with an intensity above some threshold. The remaining discussion of the alignment module relates to calibration of the optics assembly illustrated in FIG. 2, however, this discussion can be easily adapted to the other optics assemblies discussed above. The processing unit activates the micromotor so the micromotor 50 incrementally advances to filter into the transmitted beam 42. The processing unit monitors the detector elements 180 within the transmitted beam zone 38. When the monitored detector elements 180 indicate that the transmitted beam 42 is not being received, the advance of the filter is stopped. In another embodiment, opposing ends of the filter can be coupled to different micromotors which are controlled by the processing unit. When the signals from the detector elements 180 indicate that one end of the filter is in the correct position while the other end of the filter is not. The micromotors can be independently adjusted until the filter is correctly positioned.

The startup module 196 is accessed before positioning a breast 32 within the breast positioning area 12. The incident beam is formed and with any implements in place which will be used during the analysis. For instance, if a filter will be used, the filter is positioned within the formed beam. The scattering pattern module 198 is accessed to determine the scattering pattern. This initial scattering pattern is then stored in memory 190. Any detector elements 180 receiving the transmitted beam are identified by identifying the detector elements 180 receiving radiation with an intensity above some threshold. The identified detector elements 180 are stored along with the intensity received on the identified detector elements 180.

The scattering pattern module 198 determines the scattering pattern of an analysis section. The scattering pattern can be determined for each row 182 of detector elements 180 which are receiving radiation. As a result, the scattering pattern can be determined for each tested section 187. The scattering pattern for each tested section 187 is determined by finding the intensity of radiation received by each detector element in the row 182 of detector elements 180 corresponding to the tested section 187.

The intensity of radiation received by each detector element is found by counting the average number of photons received at the detector element 180 over a period of time. Increasing the number of photons received within the scattering section improves accuracy of the averages. A suitable number of photons for creating a scattering pattern is on the order of 10,000 photons received between 1 arc minutes from the center of the transmitted beam and 10 arc minutes from the center of the transmitted beam. The radiation dose required to create the scattering pattern can be calculated from the ratio of the scattered to transmitted photons.

The scattering pattern for each tested section 187 is stored in the memory 190 as the intensity at each detector element versus that detector elements 180 position in the detector 28. A final scattering pattern for each tested section 187 can be calculated by subtracting the initial scattering pattern calculated during the startup module 196 from the scattering pattern determined with the breast in place. The final scattering pattern can be determined after a scan is completed or at other times during the analysis.

The scattering pattern on opposing sides of the transmitted beam zone 38 are frequently symmetrical. Accordingly, the scattering pattern can frequently be developed by monitoring the portion of the scattering zone 40 on one side of the transmitted beam zone 38. As a result, the transmitted beam 42 can be aligned with one end of the detector as illustrated in FIG. 2.

The absorption image module 202 can be accessed when the optics assembly 18 is scanned across the breast 32 for embodiments which do not completely screen the detector from the transmitted beam. During the scan, the processing unit 189 monitors the signal from detector elements 180 within the transmitted beam zone 38. The absorption at each detector element 180 is calculated by subtracting the monitored intensity at that detector element from the intensity for that detector element 180 which was stored during the start up module. The changes in the absorption are used to develop an absorption image. The absorption image is provided to the user over the user interface 192. Since there are many rows 182 of detector elements 180 across the detector 28, the absorption image can be created for a single cross section of the breast 32 or for multiple cross sections of the breast 32.

The scattering image module 200 can be accessed when the optics assembly 18 is scanned across the breast 32. During the scan, the processing unit accesses the scattering pattern module for each analysis section. After the scan is completed, the substance identification module can access the substance identification module to determine the substances within each tested section of the scan. The results are used to determine a scattering image which is provided to the user over the user interface.

The scattering image can be used alone or in combination with the absorption image. For instance, tissues with similar absorptions are very difficult to distinguish on an absorption image. However, these tissue will likely have different scattering patterns and will show up as different tissues on the scattering image.

The scattering image can be formed without the need for breast compression. When the breast 32 is not compressed, the quality of the scattering image can be increased by compensating for changes in the thickness of the breast 32. A relationship exists between the absorption of various substances and the quantity of substance in the tested section 187. Accordingly, an approximate thickness of the tested section 187 can be determined from the absorption of the tested section 187. Each point of the scattering image can be formed be taking into account the thickness of the breast at that point.

The substance identification module 204 can be accessed when a discrete analysis section is tested or when the optics assembly 18 is scanned over the breast 32. The substance identification module 204 identifies the substances which make up a tested section 187. The memory 190 includes stored scattering patterns for known substances or known combinations of substances. The scattering pattern for each tested section 187 is compared with each of the stored scattering patterns to find a match between the tested section's scattering pattern and a stored scattering pattern or a combination of stored scattering patterns. When a high quality match is found, the substance composition of the tested section 187 is characterized as having a similar composition as the stored scattering pattern. When a high quality match is not found, different combinations of stored scattering patterns can be superimposed to find a match with the determined scattering pattern. When a match is found, the substance composition of the tested section 187 can be characterized as having a similar composition as the substances used to make up the superpositions of scattering patterns.

When the tissue identification module 204 indicates a possibility of malignant tissues, a biopsy can be used to verify the results. The result from the biopsy can be stored in the memory 190 along with the scattering pattern for future comparisons.

Figure 15:
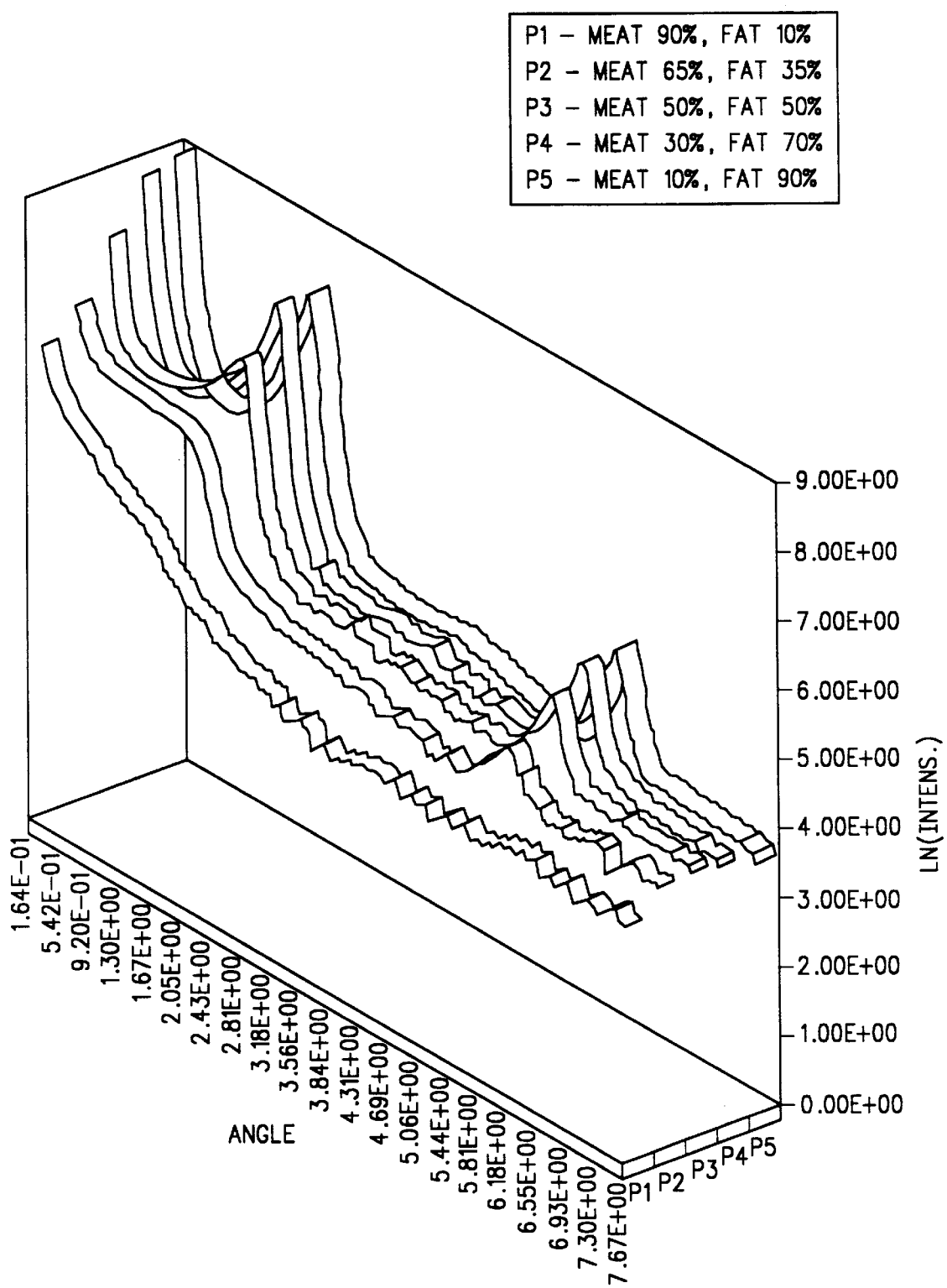
FIG. 15 is a plot of the intensity versus the scattering angle for a sample of meat with different fat content.

The substance quantization module 206 can be accessed when a discrete analysis section is tested or when the optics assembly 18 is scanned over the breast 32. This module 206 determines the quantity of each substance in the tested section 187. FIG. 15 illustrates how a scattering pattern changes with increased proportion of fat in the tissue. The intensity of the peaks increases with the increasing fat content. Accordingly, there is a relationship between the proportion of a substance in the tested section 187 and the scattering pattern peak intensity. Once the substances which make up a tested section 187 are identified, the substance quantization modules 206 analyzes the intensity of the peaks in the tested section's scattering pattern to identify the proportion of each substance in the tested section 187.

The substance quantization module 206 can also determine the absolute amount of a substance in a tested section 187. The determination is made by knowing the proportion of a substance in the tested section 187 and knowing the size of the tested section 187. The size of the tested section 187 is determined from the thickness of the breast 32 at the tested section 187. In embodiments where the breast positioning area 12 includes plates for compressing the breast 32, the displacement of the plates during the compression is the thickness of the breast 32. As discussed above, an approximate thickness of the tested section 187 can also be determined from the absorption of the tested section 187. This thickness can also be used in determining the absolute amount of a substance in the analysis section.

Figure 16:
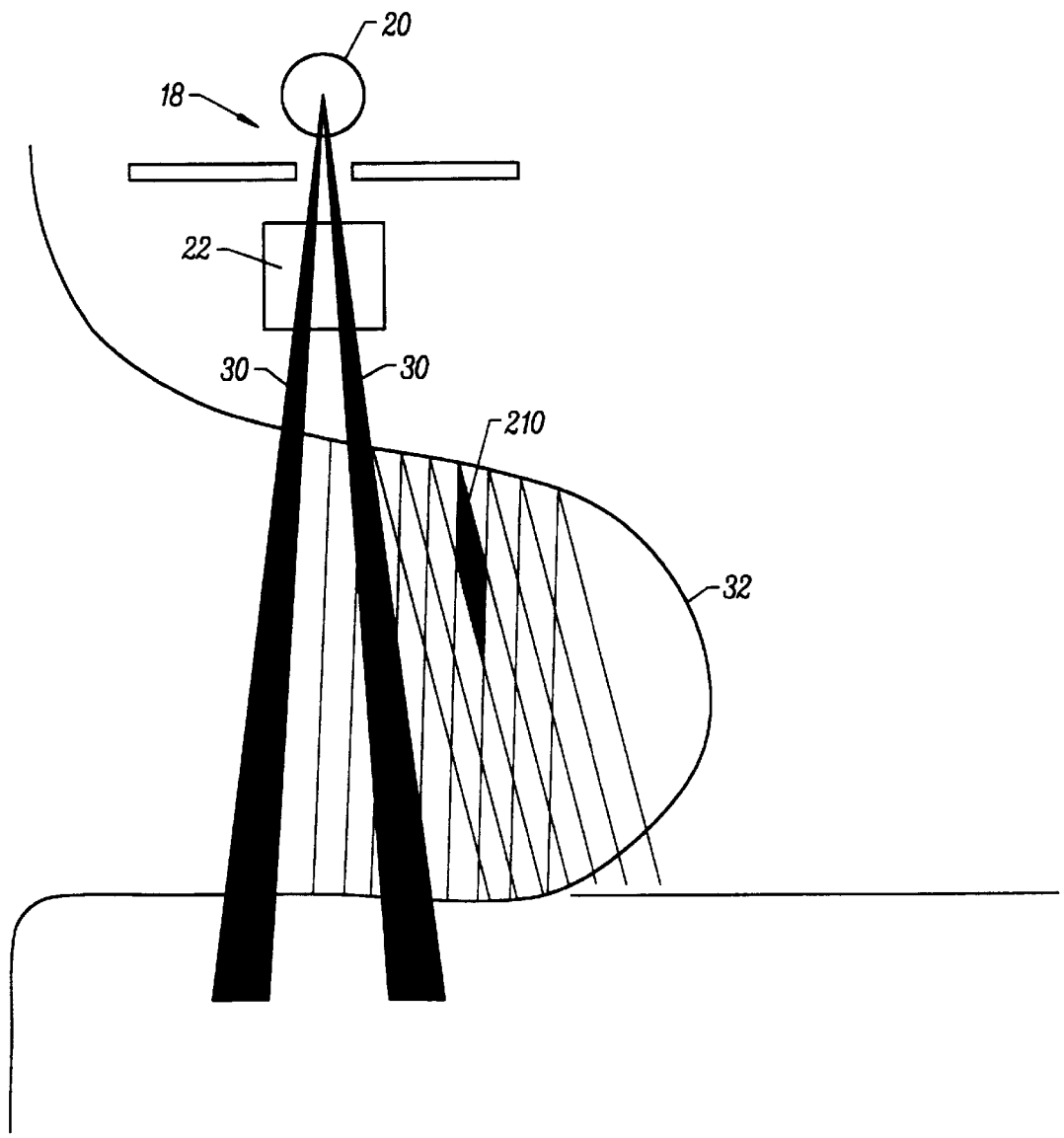
FIG. 16 illustrates the breast sections which are defined by two incident beams which are incident on the breast at different angles being scanned across the breast.

The substance positioning module 208 can be accessed when the optics assembly 18 includes a plurality of incident beams 30 which are incident on the breast 32 at different angles. A scan of the breast 32 done by two incident beams 30 at different angles can result in two sets of analysis sections. As illustrated in FIG. 16, the analysis sections corresponding to each incident beam 30 overlap to form a matrix of breast sections 210. The processing unit 189 accesses the substance identification module to determine the substances present in each tested section. Tomography software can then be used to determine the substances within each breast section and to construct a three dimensional image of the breast with the correct positioning of the substances within the breast.

Figure 17:
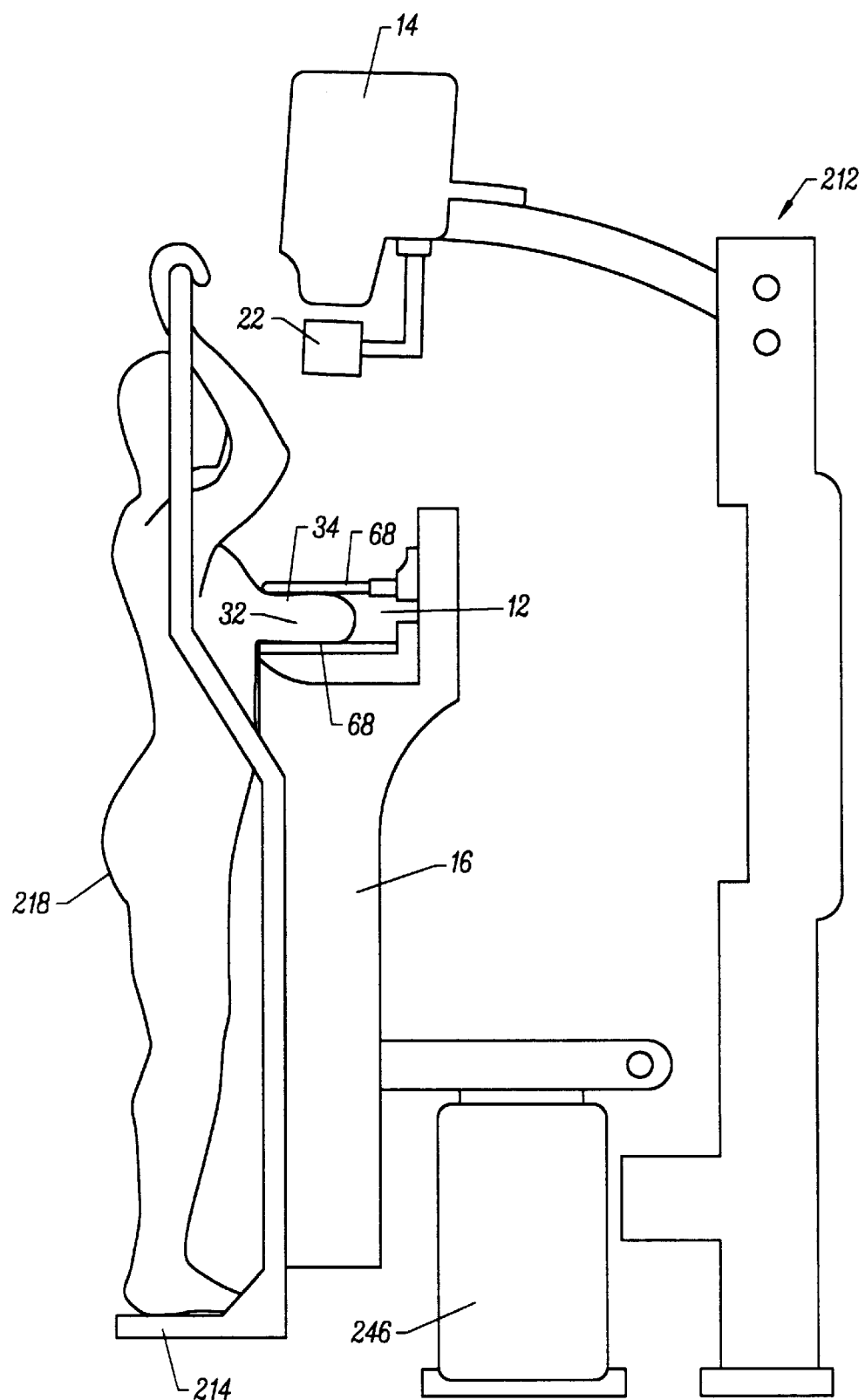
FIG. 17 is a sideview of a mammography apparatus including an optics assembly according to the present invention.

FIG. 17 illustrates an embodiment of a mammography apparatus 212 which includes the optics assembly 18. The patient stands on a platform 214 and places her breast 32 in the breast positioning area 12. Although the breast positioning area 12 illustrated provides compression to the breast 32, compression is not necessary with the present invention. The platform 214 is coupled with a hydraulic system 216. The hydraulics system moves the patient 218 relative to the optics assembly 18. The movement can be used to move the patient 218 so the incident beam(s) 30 will pass through a particular analysis section. Further, the movement can be used to scan the patient's 218 entire breast. Accordingly, a scan of the patient's 218 breast can be performed without moving the optics assembly 18. A stationary optics assembly 18 can reduce vibrations which may cause the filter 26 and beam forming apparatus 22 to become unaligned.

Figure 18:
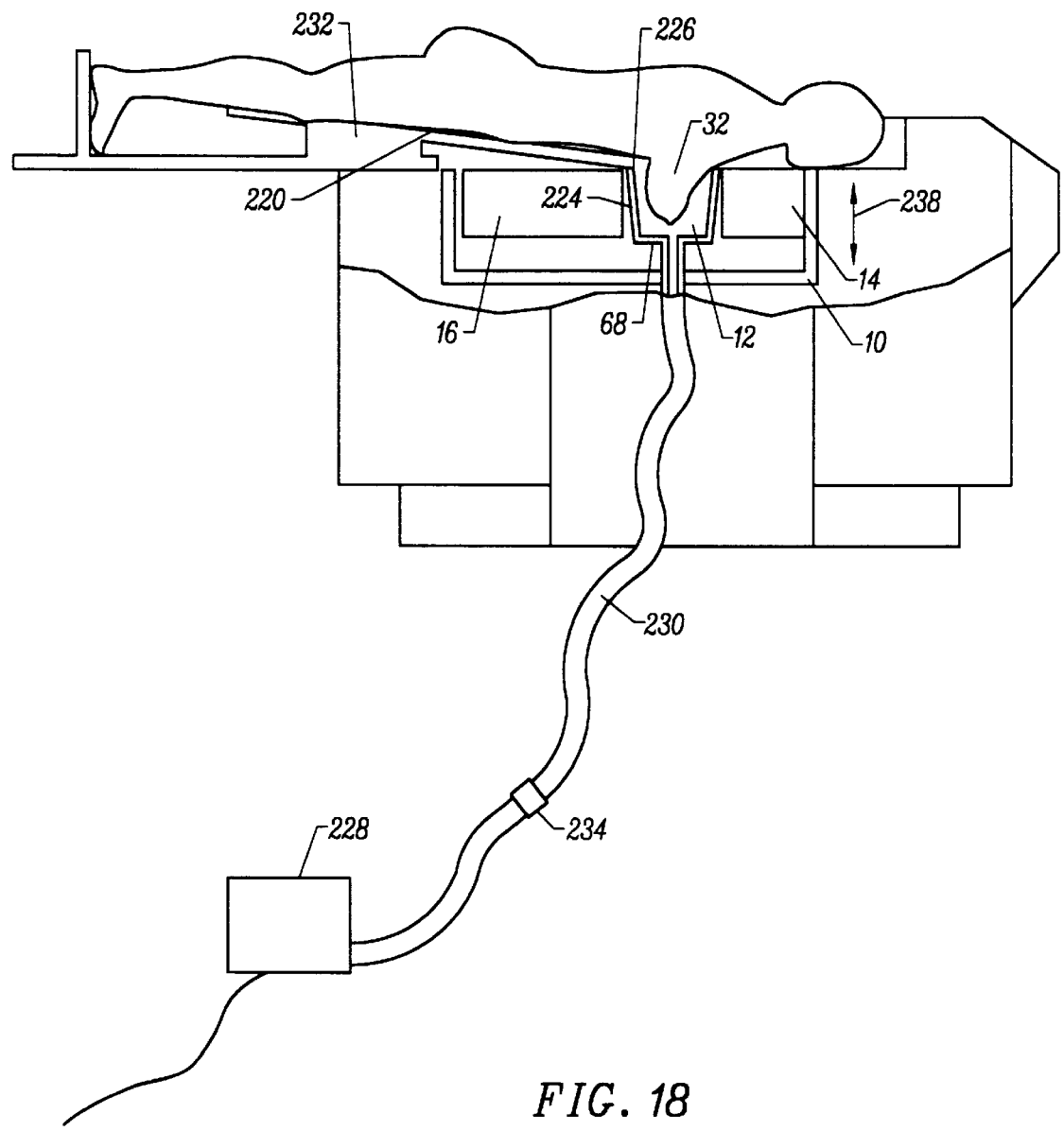
FIG. 18 is a sideview of a mammography apparatus including an optics assembly according to the present invention.

Another embodiment of a mammography apparatus 212 is illustrated in FIG. 18. The patient 218 lays on an upper surface 220 of a table 222 with her breast 32 hanging downward into the breast positioning area 12. The patient 218 can relax in this position so the breast 32 will remain stationary during the analysis. Further, the action of gravity naturally draws more of the breast 32 into the breast positioning area 12 allowing an increased portion of the breast 32 to be analyzed.

The breast positioning area 12 can be a cup 224 with an upper edge 226 designed to create a seal between the patient 218 and the cup 224. The cup 224 can be constructed from a material which is transparent to the radiation. Suitable materials include, but are not limited to, polyethylene. A vacuum source 228 and a vacuum tube 230 can be coupled to the cup 224. The vacuum source 228 is used to create a weak vacuum when the breast 32 is positioned in the holder and a seal is created between the patient 218 and the cup 224. The vacuum can serve to hold the breast 32 in a desired position and to hold the breast 32 stationary in that position. A valve 234 can be included in the vacuum connection 232. The valve 234 can release on command or when the pressure in the cup 224 exceeds a critical value.

The breast positioning area 12 need not include any structure for holding the breast. The action of gravity will serve to keep the breast still during the analysis. Further, the patient is in a comfortable position which allows her to relax and makes her less likely to move.

The frame 10 can rotate about the axis 74 of the breast 32. The rotation allows different projections of the breast 32 to be obtained. The upper housing can be move along the axis 74 of the breast 32 as indicated by the arrow 238. This motion allows the breast 32 to be positioned so the incident beam(s) 30 penetrates a particular analysis section. The motion can also be used to scan the breast 32. In another embodiment this motion is created by coupling the upper surface 220 to a lift (not shown) which can raise and lower the table 222. The lift can then be used to position the breast 32 relative to the optics assembly 18 for a scan.

A method for using the mammography apparatus 212 will now be described. A preliminary determination of whether the breast 32 has any suspicious tissues is made. The determination can be made by conventional mammography techniques or by using a scattering image or a absorption image developed by the present invention.

If the breast 32 is not already in the breast positioning area 12 of the mammography apparatus, the breast 32 is positioned in the breast positioning area 12. The optics assembly 18 and patient 218 are moved relative to one another until a desired analysis section is aligned with an incident beam 30. The desired analysis section can include tissues which are suspicious and tissue which are not suspicious.

The scattering pattern of each analysis section is obtained by radiating the analysis sections with the optics assembly 18 held in place long enough to obtain a high resolution scattering pattern. When the apparatus includes a beam forming apparatus 22 which can rotate (FIG. 4), the scattering pattern can also be obtained for a variety of azimuthal angles 88.

The scattering pattern of each analysis section is then compared with stored scattering pattern for a known tissue or for a known combination of tissues. The stored scattering patterns can be grouped into classes such as normal tissues for someone of a certain age, or normal tissue for someone with a physiological condition such as pregnancy. When a match is found between the scattering pattern of the analysis section and the stored scattering pattern or a class of stored scattering patterns, the analysis section is characterized as being comprised of the same or similar tissues as are in the stored scattering pattern or class of scattering patterns. Accordingly, when an analysis section has a scattering pattern similar to the scattering patterns for malignant cancer tissue, the analysis section is characterized as having malignant cancer tissue.

When a match is not found, a cytology analysis or biopsy can be performed to determine the substances which make up the tissue. Since the substances making up the analysis section will then be known, the scattering pattern can then be included among the stored scattering patterns.

The comparison of scattering patterns can be done by a processing unit 189 with access to a tissue identification module 204 described above. When the detector 28 is a photographic film, the comparison can be done by manually comparing the photographic film to photographic films having the scattering patterns of the known substances.

Figure 19:
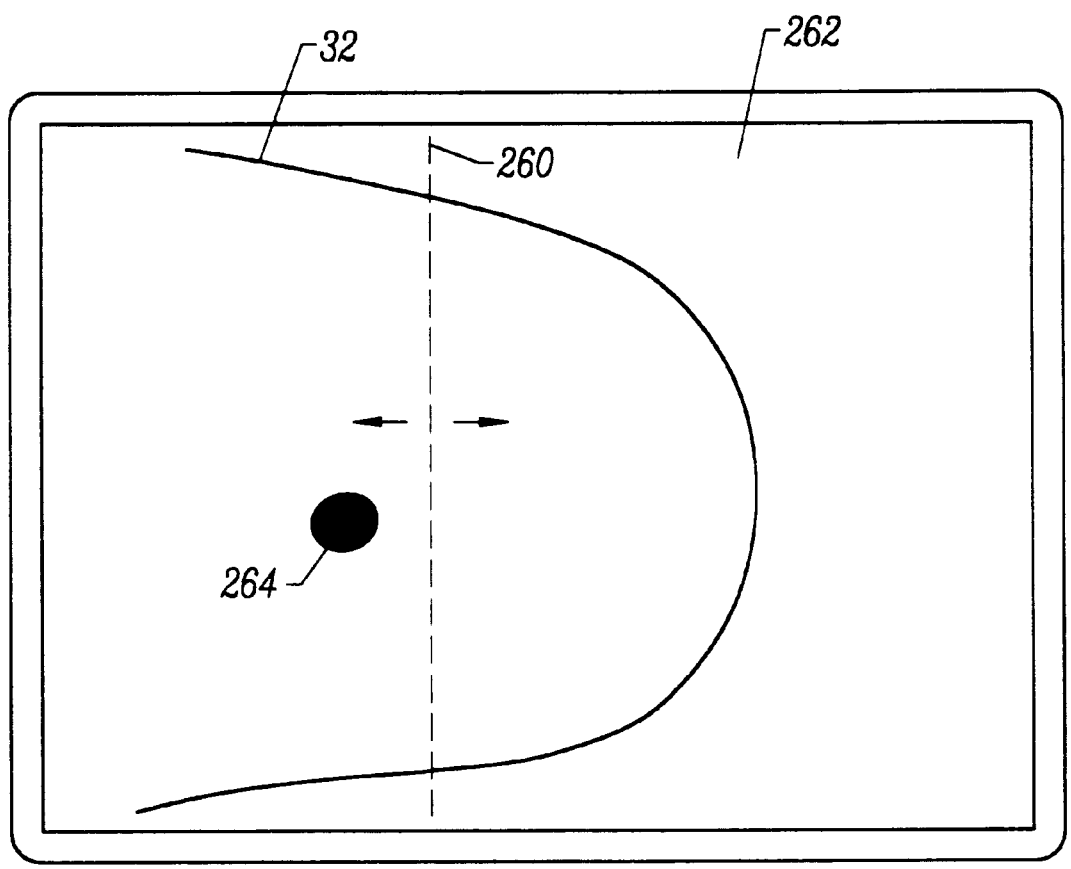
FIG. 19 illustrates a cursor on an image of the breast.

The incident beam 30 can be aligned with suspicious tissue through a number of techniques. When the preliminary determination of suspicious tissues was obtained from a scan to develop a scattering image or an absorption image, the alignment of the optics assembly 18 and analysis section can be automated by returning the optics assembly 18 to the position where the suspicious tissues were revealed during the scan. The optics assembly 18 can be manually or automatically returned to the desired position by moving the optics assembly 18 back over the breast 32 without turning on the radiation. The return can be based on a cursor 260 which is visible on the scattering or absorption image 262 as illustrated in FIG. 19. The cursor's position on the image can indicate the position of the optics assembly 18 relative to the breast 32. As a result, when the cursor is positioned adjacent the suspicious tissue 264 in the image 262, if the breast 32 has not moved, the optics assembly 18 is in the same position it was in at the time the that portion of the image 262 was created. Accordingly, the optics assembly 18 can be aligned with a desired analysis section by aligning the cursor 260 with the portion of the image which includes the suspicious tissue 264.

When the preliminary determination was not done with a scan, a sequential analysis of analysis sections can be used to align the incident beam 30 with the desired analysis section. When an analysis of an additional analysis section indicates that the analysis section includes substances which are more suspicious than the previous analysis section, the incident beam 30 can be moved in the direction of the subsequent section until a decrease in the amount of suspicious substances is identified.

The above optics assembly 18 is not limited to breast 32 tissues. Other tissues can be analyzed. For instance, the liver for liver cancer. The assembly can also be applied to tissues such as meats purchased by consumers.

While the present invention is disclosed by reference to the preferred embodiments and examples detailed above, it is to be understood that these examples are intended in an illustrative rather than limiting sense, as it is contemplated that modifications and combinations will readily occur to those skilled in the art, which modifications and combinations will be within the spirit of the invention and the scope of the appended claims.

What is claimed is:

1. An apparatus for analyzing substances within a breast, comprising:

one or more structures defining a breast receiving volume;

a beam forming apparatus having a geometry which forms breast penetrating radiation into a beam, directed toward the breast receiving volume so as to be incident on a breast positioned within the breast receiving volume, the beam configured to pass through the breast such that the breast scatters a scattered portion of the beam at a plurality of different scattering angles relative to the beam; and a detector positioned to at least partially receive the scattered portion of the beam at multiple different scattering angles, the detector producing signals indicating the scattering angle and the intensity of the radiation which is scattered at the multiple different scattering angles by the breast.

2. The apparatus of claim 1, further comprising:

a filter positioned to screen the detector from a transmitted portion of the beam, wherein the filter at least partially reduces an intensity of the transmitted portion of the beam.

3. The apparatus of claim 1, wherein:

the detector includes a plurality of detector elements which each provide a signal upon receiving a photon of the breast penetrating radiation.

4. The apparatus of claim 3, wherein at least a portion of the detector elements are positioned to receive photons of the breast penetrating radiation scattered outside the transmitted portion of the beam.

5. The apparatus of claim 3, wherein the position of the detector relative to the breast receiving volume is such that each detector element is associated with a particular range of scattering angles.

6. The apparatus of claim 3, wherein the displacement of the plurality of detector elements from the breast receiving volume is approximately 1 m.

7. The apparatus of claim 3, wherein the detector elements have a width of around 10 $\mu$m.

8. The apparatus of claim 1, wherein each signal is associated with a particular range of scattering angles.

9. The apparatus according to claim 1, wherein each signal is associated with a particular range of scattering angles including approximately 2 arc seconds.

10. The apparatus of claim 1, further comprising:

a position adjusting mechanism configured to move the detector relative to the breast receiving volume.

11. The apparatus of claim 1, wherein the beam forming apparatus and the detector is configured to be scanned over the breast receiving volume.

12. The apparatus of claim 1, wherein the beam forming apparatus and the detector is configured to be rotated about the breast receiving volume.

13. The apparatus of claim 1, wherein the detector provides signals indicating the intensity the transmitted portion of the beam.

14. The apparatus of claim 1, wherein the one or more structures includes a lower plate for supporting the breast.

15. The apparatus of claim 1, wherein the one or more structures includes a lower plate for supporting the breast and an upper plated for compressing the breast.

16. The apparatus of claim 1, wherein the one or more structures includes a cup.

17. The apparatus of claim 1, wherein the beam forming apparatus forms the breast penetrating radiation into one or more additional beams directed toward the breast receiving volume so as to be incident on the breast.

18. A apparatus for analyzing substances within a breast, comprising:

one or more structures defining a breast receiving volume;

a beam forming apparatus having a geometry which forms breast penetrating radiation into a plurality of beams, directed toward the breast receiving volume such that at least one of the plurality of beams is incident on a breast positioned within the breast receiving volume, the plurality of beams configured to pass through the breast such that the breast scatters a scattered portion of each beam at a plurality of different scattering angles relative to the beam from which the radiation is scattered;

a detector positioned to at least partially receive the scattered portion of one or more of the plurality of beams at multiple different scattering angles, the detector producing signals indicating the scattering angle and the intensity of the radiation from one or more of the plurality of beams which is scattered at the multiple different scattering angles by the breast.

19. The apparatus of claim 18, further comprising:

a filter positioned to screen the detector from a transmitted portion of one or more of the plurality of beams, wherein the filter at least partially reduces an intensity of the transmitted portion of one or more of the plurality of beams.

20. The apparatus of claim 18, wherein:

the detector includes a plurality of detector elements which each provide a signal upon receiving a photon of the breast penetrating radiation.

21. The apparatus of claim 20, wherein at least a portion of the detector elements are positioned to receive photons of the breast penetrating radiation scattered outside the transmitted portion of the beam.

22. The apparatus of claim 20, wherein the position of the detector relative to the breast receiving volume is such that each detector element is associated with a particular range of scattering angles.

23. The apparatus of claim 20, wherein the displacement of the plurality of detector elements from the breast receiving volume is approximately 1 m.

24. The apparatus of claim 20, wherein the detector elements have a width of around 10 $\mu$m.

25. The apparatus of claim 18, wherein each signal is associated with a particular range of scattering angles.

26. The apparatus according to claim 18 wherein each signal is associated with a particular ranges of scattering angles, the range of scattering angles covering 2 arc seconds.

27. The apparatus of claim 18, further comprising:

a position adjusting mechanism configured to move the detector relative to the breast receiving volume.

28. The apparatus of claim 18, wherein the beam forming apparatus and the detector is configured to be scanned over the breast receiving volume.

29. The apparatus of claim 18, wherein the beam forming apparatus and the detector is configured to be rotated about the breast receiving volume.

30. The apparatus of claim 18, wherein the detector provides signals indicating the intensity of a portion of the beam transmitted through a breast without being scattered by the breast.

31. The apparatus of claim 18, wherein the one or more structures includes a lower plate for supporting the breast.

32. The apparatus of claim 18, wherein the one or more structures includes a lower plate for supporting the breast and an upper plate for compressing the breast.

33. The apparatus of claim 18, wherein the one or more structures includes a cup.

* * * * *